United States Patent [19]

Ohtuka et al.

[11] Patent Number: 5,095,016

[45] Date of Patent: Mar. 10, 1992

[54] BENZOPYRAN COMPOUNDS, PROCESSES FOR THEIR PRODUCTION AND PHARMACEUTICAL COMPOSITIONS

[75] Inventors: Katuyuki Ohtuka, Nagareyama; Nobuo Ishiyama, Kusatsu; Yasuhito Iida, Otsu; Kenji Seri, Yashio; Takeshi Murai, Fujimi; Kazuko Sanai, Wako; Yoshihiro Ishizaka, Tokyo, all of Japan

[73] Assignee: Kaken Pharmaceutical Co., Ltd., Tokyo, Japan

[21] Appl. No.: 562,577

[22] Filed: Aug. 3, 1990

[30] Foreign Application Priority Data

Aug. 11, 1989 [JP] Japan .................... 1-208547
Dec. 29, 1989 [JP] Japan .................... 1-341528
Mar. 23, 1990 [JP] Japan .................... 2-73653
Mar. 23, 1990 [JP] Japan .................... 2-73654

[51] Int. Cl.$^5$ .................. A61K 31/35; A61K 31/535; C07D 311/68; C07D 405/10
[52] U.S. Cl. .................. 514/233.5; 514/456; 549/404; 549/399; 544/151
[58] Field of Search .................. 549/404, 399; 544/151; 514/456, 233.5

[56] References Cited

FOREIGN PATENT DOCUMENTS 176689 4/1986 European Pat. Off. .
214818 3/1987 European Pat. Off. .
344747 12/1989 European Pat. Off. .
89/10925 11/1989 World Int. Prop. O. .

OTHER PUBLICATIONS

Journal of Medicinal Chemistry, vol. 26, No. 11, 1983, Columbus, Ohio, pp. 1582-1589; John M. Evans et al.: "Synthesis and Antihypertensive Activity of Substituted trans-4-Amino-3,4-dihydro-2,2-dimethyl-2-H-1-benzopyran-3-ols".
Journal of Medicinal Chemistry, vol. 21, No. 8, 1978, Columbus, Ohio, pp. 733-781; Hans Jorgen Peterson etc.: "Synthesis and Hypotensive Activity of N-Alkyl-N''-cyano-N'-pyridylguanidines".

Primary Examiner—Nicky Chan
Attorney, Agent, or Firm—Oblon, Spivak, McClelland, Maier & Neustadt

[57] ABSTRACT

A compound of the formula (I):

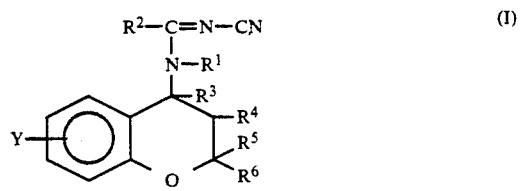

or a pharmaceutically acceptable salt thereof, wherein:
$R^1$ is a hydrogen atom, a substituted or unsubstituted $C_{1-6}$ alkyl group, a $C_{2-6}$ alkenyl group, a $C_{2-6}$ alkynyl group or a $R^7$—CO— group (wherein $R^7$ is a $C_{1-6}$ alkyl group, a phenyl group, a $C_{2-6}$ alkenyl group which may be substituted by a phenyl group, or a $C_{1-6}$ alkoxy group);
$R^2$ is a hydrogen atom, a substituted or unsubstituted $C_{1-8}$ alkyl group, or a phenyl group;
$R^3$ is a hydrogen atom, and $R^4$ is a hydroxyl group, or $R^3$ and $R^4$ together form a bond;
each of $R^5$ and $R^6$ is a $C_{1-4}$ alkyl group; and
Y is a cyano group, a halogen atom, a nitro group, a $C_{1-6}$ alkyl group, a $C_{2-6}$ alkynyl group, a $C_{1-6}$ alkylcarbonyl group, a $C_{1-6}$ alkoxy group, a di-$C_{1-6}$ alkylaminocarbonyl group, an aryl group, a $C_{1-6}$ alkoxycarbonyl group, a carboxyl group or a morpholinocarbonyl group.

8 Claims, No Drawings

BENZOPYRAN COMPOUNDS, PROCESSES FOR THEIR PRODUCTION AND PHARMACEUTICAL COMPOSITIONS

The present invention relates to novel benzopyran compounds, processes for their production and pharmaceutical compositions comprising such benzopyran compounds as active ingredients.

In recent years, as old aged population increases an attention has been drawn to hypertension which can be a serious dangerous factor to health. As agents for treating such hypertension, many drugs having various types of active mechanisms have been widely clinically used. From now on, it is desired to develop new hypotensive drugs having potassium channel activating action having superior active mechanisms.

It is an object of the present invention to provide novel compounds which have excellent potassium channel activating action and thus are useful for treatment of various diseases.

The present inventors have synthesized novel benzopyran derivatives and have studied potassium channel activating action thereof and have found that the benzopyran compounds of the following formula (I) have excellent potassium channel activating action and exhibit strong blood pressure lowering activities and bronchodilator activities due to such active mechanisms. Thus, the above object has been accomplished.

The present invention provides a benzopyran compound of the formula (I):

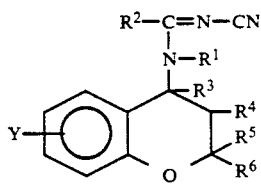
(I)

or a pharmaceutically acceptable salt thereof, wherein:

$R^1$ is a hydrogen atom, a substituted or unsubstituted $C_{1-6}$ alkyl group, a $C_{2-6}$ alkenyl group, a $C_{2-6}$ alkynyl group or a $R^7$—CO— group (wherein $R^7$ is a $C_{1-6}$ alkyl group, a phenyl group, a $C_{2-6}$ alkenyl group which may be substituted by a phenyl group, or a $C_{1-6}$ alkoxy group);

$R^2$ is a hydrogen atom, a substituted or unsubstituted $C_{1-8}$ alkyl group, or a phenyl group;

$R^3$ is a hydrogen atom, and $R^4$ is a hydroxyl group, or $R^3$ and $R^4$ together form a bond;

each of $R^5$ and $R^6$ is a $C_{1-4}$ alkyl group; and

Y is a cyano group, a halogen atom, a nitro group, a $C_{1-6}$ alkyl group, a $C_{2-6}$ alkynyl group, a $C_{1-6}$ alkylcarbonyl group, a $C_{1-6}$ alkoxy group, a di-$C_{1-6}$ alkylaminocarbonyl group, an aryl group, a $C_{1-6}$ alkoxycarbonyl group, a carboxyl group or a morpholinocarbonyl group.

The present invention also provides a process for producing the compound of the formula (I) or a pharmaceutically acceptable salt thereof, which comprises:

(1) reacting a compound of the formula (II):

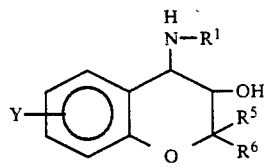
(II)

wherein $R^1$, $R^5$, $R^6$ and Y are as defined above provided that $R^1$ being a $R^7$—CO— group and Y being a carboxyl group are excluded, with a compound of the formula (III):

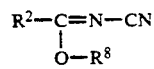
(III)

wherein $R^2$ is as defined above, and $R^8$ is a $C_{1-6}$ alkyl group, to obtain a compound of the formula (I) wherein $R^3$ is a hydrogen atom and $R^4$ is a hydroxyl group;

(2) reacting a compound of the formula

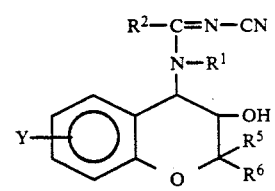
(Ia)

wherein $R^1$, $R^2$, $R^5$, $R^6$ and Y are as defined above provided that $R^1$ being a $R^7$—CO— group and Y being a carboxyl group are excluded, with a compound of the formula (IV):

$$R^9SO_2X \qquad (IV)$$

wherein $R^9$ is an alkyl group or a substituted or unsubstituted aryl group, and X is a halogen atom, to form a compound of the formula (V):

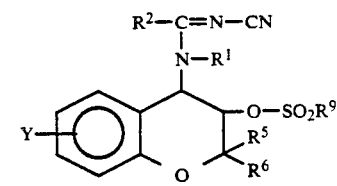
(V)

where $R^1$, $R^2$, $R^5$, $R^6$, $R^9$ and Y are as defined above, and then treating the compound of the formula (V) with a compound of the formula (VI):

$$R^{10}OM \qquad (VI)$$

wherein $R^{10}$ is an alkyl group, and M is an alkali metal, to obtain a compound of the formula (I) wherein $R^3$ and $R^4$ together form a bond;

(3) reacting the compound of the formula (V) with 1,8-diazabicyclo[5,4,0]-7-undecene, to obtain a compound of the formula (I) wherein $R^3$ and $R^4$ together form a bond;

(4) treating the compound of the formula (Ia) with sodium hydride, hydrochloric acid or p-toluenesulfonic acid for dehydration, to obtain a compound of the formula (I) wherein $R^3$ and $R^4$ together form a bond;

(5) reacting the compound of the formula (VII):

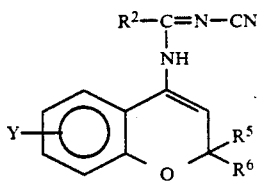

(VII)

wherein $R^2$, $R^5$, $R^6$ and Y are as defined above, with a compound of the formula (VIII):

$$R^{11}—X \quad \text{(VIII)}$$

wherein $R^{11}$ is a substituted or unsubstituted $C_{1-6}$ alkyl group, a $C_{2-6}$ alkenyl group, a $C_{2-6}$ alkynyl group, and X is a halogen atom, to obtain a compound of the formula (I) wherein $R^1$ is a substituted or unsubstituted $C_{1-6}$ alkyl, a $C_{2-6}$ alkenyl group, a $C_{2-6}$ alkynyl group, and $R^3$ and $R^4$ together form a bond;

(6) reacting the compound of the formula (VII) with a compound of the formula (IX):

$$R^7—CO—X \quad \text{(IX)}$$

wherein $R^7$ and X are as defined above, to obtain a compound of the formula (I) wherein $R^1$ is a $R^7$—CO— group, (wherein $R^7$ is a defined above), and $R^3$ and $R^4$ together form a bond;

(7) hydrolyzing a compound of the formula (X):

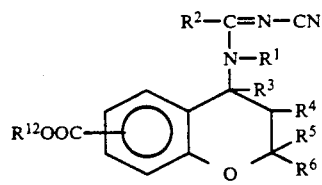

(X)

wherein $R^1$, $R^2$, $R^3$, $R^4$, $R^5$ and $R^6$ are as defined above, $R^{12}$ is a $C_{1-6}$ alkyl group, to obtain a compound of the formula (I) wherein Y is a carboxyl group; or (8) reacting a compound of the formula (I) wherein Y is a carboxyl group, with morpholine or a dialkylamine, to obtain a compound of the formula (I) wherein Y is morpholinocarbonyl group or a di-$C_{1-6}$ alkylaminocarbonyl group.

Further, the present invention provides a pharmaceutical composition having a potassium channel activating action, which comprises a compound of the formula (I) or a pharmaceutically acceptable salt thereof, as an active ingredient.

The present invention further provides a hypotensive or anti-asthma drug which comprises a compound of the formula (I) or a pharmaceutically acceptable salt thereof as an active ingredient.

Still further, the present invention provides a $C_{2-6}$ alkynyl-3,4-dihydro-2,2-dimethyl-trans-4-amino-2H-benzo[b]pyran-3-ol as an intermediate and as a novel compound.

Now, the present invention will be described in detail with reference to the preferred embodiments.

In the formula (I) representing the benzopyran compounds of the present invention, the $C_{1-6}$ alkyl group for $R^1$, $R^7$ and Y includes, for example, a methyl group, an ethyl group, a propyl group, an iso-propyl group, a n-butyl group, a sec butyl group, a tert butyl group, a pentyl group and a hexyl group. Likewise, the $C_{1-4}$ alkyl group for $R^5$ or $R^6$ includes, for example, a methyl group, an ethyl group, a propyl group, an iso-propyl group, a n-butyl group, a sec-butyl group and a tert-butyl group. The $C_{1-8}$ alkyl group for $R^2$ includes, for example, a methyl group, an ethyl group, a propyl group, an isopropyl group, a n-butyl group, a sec-butyl group, a tert-butyl group, a pentyl group, a hexyl group, a heptyl group and an octyl group. The $C_{2-6}$ alkenyl group for $R^1$ or $R^7$ includes, for example, an allyl group, a methallyl group, a crotyl group, a 1-methylallyl group, a prenyl group, a 3-methyl-3-butenyl group and a 3-pentenyl group. The $C_{2-6}$ alkynyl group for $R^1$ or Y includes, for example, an ethynyl group, a propargyl group, a 1-methylpropagyl group, a 2-butynyl group, a 1-methyl-2-butynyl group, a 3-butynyl group, a 2-pentynyl group and a 3-pentynyl group. The $C_{1-6}$ alkoxy group for $R^7$ or Y includes, for example, a methoxy group, an ethoxy group, a propoxy group, an iso-propoxy group, a n-butoxy group, a sec-butoxy group, a tert-butoxy group, a pentyloxy group and a hexyloxy group.

The substituent for the substituted $C_{1-6}$ alkyl group for $R^1$ may be a $C_{1-6}$ alkoxy group, an aryl group, a hydroxyl group, a $C_{1-6}$ alkoxycarbonyl group or a di-$C_{1-6}$ alkylamino group. The $C_{1-6}$ alkoxy group as such a substituent includes, for example, a methoxy group, an ethoxy group, a propoxy group, an iso-propoxy group, a n-butoxy group, a sec-butoxy group, a tert-butoxy group, a pentyloxy group and a hexyloxy group. The aryl group includes, for example, a phenyl group, a naphthyl group and a xylyl group. The $C_{1-6}$ alkoxycarbonyl group includes, for example, a methoxycarbonyl group, an ethoxycarbonyl group, a propoxycarbonyl group, an iso-propoxycarbonyl group, a n-butoxycarbonyl group, a sec-butoxycarbonyl group, a tert-butoxycarbonyl group, a pentyloxycarbonyl group and a hexyloxycarbonyl group. The $C_{1-6}$ alkyl group in the di-$C_{1-6}$ alkylamino group includes, for example, a methyl group, an ethyl group, a propyl group, an iso-propyl group, a n-butyl group, a sec-butyl group, a tert-butyl group, a pentyl group and a hexyl group.

The substituent for the substituted $C_{1-8}$ alkyl group for $R^2$ may be a $C_{1-6}$ alkoxy group or an aryl group. The $C_{1-6}$ alkoxy group as such a substituent includes, for example, a methoxy group, an ethoxy group, a propoxy group, an iso-propoxy group, a n-butoxy group, a sec-butoxy group, a tert-butoxy group, a pentyloxy group and a hexyloxy group. The aryl group includes, for example, a phenyl group, a naphthyl group and a xylyl group.

The halogen atom for Y includes, for example, a chlorine atom, a fluorine atom and an iodine atom. The $C_{1-6}$ alkoxycarbonyl group includes, for example, a methoxycarbonyl group, an ethoxycarbonyl group, a propoxycarbonyl group, an iso-propoxycarbonyl group, a n-butoxycarbonyl group, a sec-butoxycarbonyl group, a tert-butoxycarbonyl group, a pentyloxycarbonyl group and a hexyloxycarbonyl group. The $C_{1-6}$ alkylcarbonyl group includes, for example, a methylcarbonyl group, an ethylcarbonyl group, a propylcarbonyl group, a butylcarbonyl group, a pentylcarbonyl group and a hexylcarbonyl group. The di-$C_{1-6}$ alkylaminocarbonyl group includes, for example, a dimethylaminocarbonyl group and a diethylaminocarbonyl group. The aryl group includes, for example, a phenyl group, a naphthyl group and a xylyl group.

In addition to those given in the Examples presented hereinafter, the following compounds may be mentioned as preferred compounds of the formula (I).

(1) 6-cyano-2,2-dimethyl-4-[(N-cyano-butyrimidoyl)amino]-2H-benzo[b]pyran
(2) 6-cyano-2,2-dimethyl-4-[(N-cyano-isobutyrimidoyl)amino]-2H-benzo[b]pyran
(3) 6-cyano-2,2-dimethyl-4-[(N-cyano-isovalerimidoyl)amino]-2H-benzo[b]pyran
(4) 6-cyano-2,2-dimethyl-4-[ (N-cyano-methylethylacetimidoyl)amino[-2H-benzo[b]pyran
(5) 6-cyano-2,2-dimethyl-4-[(N-cyano-pivalimidoyl)amino]-2H-benzo[b]pyran
(6) 6-cyano-2,2-dimethyl-4-[(N-cyano-hexanimidoyl)amino]-2H-benzo[b]pyran
(7) 6-cyano-2,2-dimethyl-4-[(N-cyano-heptanimidoyl)amino]-2H-benzo[b]pyran
(8) 6-cyano-2,2-dimethyl-4-[(N-cyano-2-phenylacetimidoyl)amino]-2H-benzo[b]pyran
(9) 6-cyano-2,2-dimethyl-4-[(N-cyano-3-phenylpropionimidoyl)amino]-2H-benzo[b]pyran
(10) 6-cyano-2,2-dimethyl-4-[N-methyl-(N-cyano-formimidoyl)amino]-2H-benzo[b]pyran
(11) 6-cyano-2,2-dimethyl-4-[N-methyl-(N-cyano-acetimidoyl)amino]-2H-benzo[b]pyran
(12) 6-cyano-2,2-dimethyl-4-[N-methyl-(N-cyano-propionimidoyl)amino]-2H-benzo[b]pyran
(13) 6-cyano-2,2-dimethyl-4-[N-methyl-(N-cyano-butyrimidoyl)amino]-2H-benzo[b]pyran
(14) 6-cyano-2,2-dimethyl-4-[N-methyl-(N-cyano-benzimidoyl)amino]-2H-benzo[b]pyran
(15) 6-cyano-2,2-dimethyl-4-[N-ethyl-(N-cyano-formimidoyl)amino]-2H-benzo[b]pyran
(16) 6-cyano-2,2-dimethyl-4-[N-ethyl-(N-cyano-acetimidoyl)amino]-2H-benzo[b]pyran
(17) 6-cyano-2,2-dimethyl-4-[N-ethyl-(N-cyano-propionimidoyl)amino]-2H-benzo[b]pyran
(18) 6-cyano-2,2-dimethyl-4-[N-ethyl-(N-cyano-benzimidoyl)amino]-2H-benzo[b]pyran
(19) 6-cyano-2,2-dimethyl-4-[N-propyl-(N-cyano-formimidoyl)amino]-2H-benzo[b]pyran
(20) 6-cyano-2,2-dimethyl-4-[N-propyl-(N-cyano-acetimidoyl)amino]-2H-benzo[b]pyran
(21) 6-cyano-2,2-dimethyl-4-[N-propyl-(N-cyano-benzimidoyl)amino]-2H-benzo[b]pyran
(22) 6-cyano-2,2-dimethyl-4-[(N-cyano-2-methoxyacetimidoyl)amino]-2H-benzo[b]pyran
(23) 6-cyano-2,2-dimethyl-4-[(N-cyano-3-methoxypropionimidoyl)amino]-2H-benzo[b]pyran
(24) 6-cyano-2,2-dimethyl-4-[N-butyl-(N-cyano-formimidoyl)amino]-2H-benzo[b]pyran
(25) 6-cyano-2,2-dimethyl-4-[N-butyl-(N-cyano-acetimidoyl)amino]-2H-benzo[b]pyran
(26) 6-cyano-2,2-dimethyl-4-[N-benzyl-(N-cyano-formimidoyl)amino]-2H-benzo[b]pyran
(27) 6-cyano-2,2-dimethyl-4-[N-benzyl-(N-cyano-acetimidoyl)amino]-2H-benzo[b]pyran
(28) 6-cyano-2,2-dimethyl-4-[N-allyl-(N-cyano-formimidoyl)amino]-2H-benzo[b]pyran
(29) 6-cyano-2,2-dimethyl-4-[N-allyl-(N-cyano-acetimidoyl)amino]-2H-benzo[b]pyran
(30) 6-cyano-2,2-dimethyl-4-[N-2-methoxyethyl-(N-cyano-formimidoyl)amino]-2H-benzo[b]pyran
(31) 6-cyano-2,2-dimethyl-4-[N-2-methoxyethyl-(N-cyano-acetimidoyl)amino] -2H-benzo[b]pyran
(32) 6-cyano-2,2-dimethyl-4-[N-propargyl-(N-cyano-formimidoyl)amino]-2H-benzo[b]pyran
(33) 6-cyano-2,2-dimethyl-4-[N-propargyl-(N-cyano-acetimidoyl)amino]-2H-benzo[b]pyran
(34) 6-nitro-2,2-dimethyl-4-[(N-cyano-acetimidoyl)amino]-2H-benzo[b]pyran
(35) 6-cyano-3,4-dihydro-2,2-dimethyl-trans-4-[(N-cyano-isobutyrimidoyl)amino]-2H-benzo[b]pyran-3-ol
(36) 6-cyano-3,4-dihydro-2,2-dimethyl-trans-4-[(N-cyano-isovalerimidoyl)amino]-2H-benzo[b]pyran-3-ol
(37) 6-cyano-3,4-dihydro-2,2-dimethyl-trans-4-[(N-cyano-methylethylacetimidoyl)amino]-2H-benzo[b]pyran-3-ol
(38) 6-cyano-3,4-dihydro-2,2-dimethyl-trans-4-[(N-cyano-pivalimidoyl)amino]-2H-benzo[b]pyran-3-ol
(39) 6-cyano-3,4-dihydro-2,2-dimethyl-trans-4-[(N-cyano-hexanoimidoyl)amino]-2H-benzo[b]pyran-3-ol
(40) 6-cyano-3,4-dihydro-2,2-dimethyl-trans-4-[(N-cyano-heptanoimidoyl)amino]-2H-benzo[b]pyran-3-ol
(41) 6-cyano-3,4-dihydro-2,2-dimethyl-trans-4-[(N-cyano-2-methoxyacetimidoyl)amino]-2H-benzo[b]pyran-3-ol
(42) 6-cyano-3,4-dihydro-2,2-dimethyl-trans-4-[(N-cyano-3-methoxypropionimidoyl)amino]-2H-benzo[b]pyran-3-ol
(43) 6-cyano-3,4-dihydro-2,2-dimethyl-trans-4-[(N-cyano-2-phenylacetimidoyl)amino]-2H-benzo[b]pyran-3-ol
(44) 6-cyano-3,4-dihydro-2,2-dimethyl-trans-4-[(N-cyano-3-phenylpropionimidoyl)amino]-2H-benzo[b]pyran-3-ol
(45) 6-cyano-3,4-dihydro-2,2-dimethyl-trans-4-[N-methyl-(N-cyano-formimidoyl)amino]-2H-benzo[b]pyran-3-ol
(46) 6-cyano-3,4-dihydro-2,2-dimethyl-trans-4-[N-methyl-(N-cyano-propionimidoyl)amino]-2H-benzo[b]pyran-3-ol
(47) 6-cyano-3,4-dihydro-2,2-dimethyl-trans-4-[N-methyl-(N-cyano-butyrimidoyl)amino]-2H-benzo[b]pyran-3-ol
(48) 6-cyano-3,4-dihydro-2,2-dimethyl-trans-4-[N-methyl-(N-cyano-benzimidoyl)amino]-2H-benzo[b]pyran-3-ol
(49) 6-cyano-3,4-dihydro-2,2-dimethyl-trans-4-[N-ethyl-(N-cyano-formimidoyl)amino]-2H-benzo[b]pyran-3-ol
(50) 6-cyano-3,4-dihydro-2,2-dimethyl-trans-4-[N-ethyl-(N-cyano-acetimidoyl)amino]-2H-benzo[b]pyran-3-ol
(51) 6-cyano-3,4-dihydro-2,2-dimethyl-trans-4-[N-ethyl-(N-cyano propionimidoyl)amino]-2H-benzo[b]pyran-3-ol
(52) 6-cyano-3,4-dihydro-2,2-dimethyl-trans-4-[N-ethyl-(N-cyano-benzimidoyl)amino]-2H-benzo[b]pyran-3-ol
(53) 6-cyano-3,4-dihydro-2,2-dimethyl-trans-4-[N-propyl-(N-cyano-formimidoyl)amino]-2H-benzo[b]pyran-3-ol
(54) 6-cyano-3,4-dihydro-2,2-dimethyl-trans-4-[N-propyl-(N-cyano-acetimidoyl)amino]-2H-benzo[b]pyran-3-ol
(55) 6-cyano-3,4-dihydro-2,2-dimethyl-trans-4-[N-propyl-(N-cyano-benzimidoyl)amino]-2H-benzo[b]pyran-3-ol
(56) 6-cyano-3,4-dihydro-2,2-dimethyl-trans-4-[N-butyl-(N-cyano-formimidoyl)amino]-2H-benzo[b]pyran-3-ol

(57) 6-cyano-3,4-dihydro-2,2-dimethyl-trans-4-[N-benzyl-(N-cyano-formimidoyl)amino]-2H-benzo[b]pyran-3-ol
(58) 6-cyano-3,4-dihydro-2,2-dimethyl-trans-4-[N-allyl-(N-cyano-formimidoyl) amino]-2H-benzo[b]pyran-3-ol
(59) 6-cyano-3,4-dihydro-2,2-dimethyl-trans-4-[N-2-methoxyethyl-(N -cyano-formimidoyl)amino]-2H-benzo[b]pyran-3-ol
(60) 6-cyano-3,4-dihydro-2,2-dimethyl-trans-4-[N-2-methoxyethyl-(N -cyano-acetimidoyl)amino]-2H-benzo[b]pyran-3-ol
(61) 6-cyano-3,4-dihydro-2,2-dimethyl-trans-4-[N-propargyl-(N-cyano-formimidoyl)amino]-2H-benzo[b]pyran-3-ol
(62) 6-cyano-3,4-dihydro-2,2-dimethyl-trans-4-[N-2-hydroxyethyl-(N -cyano-formimidoyl)amino]-2H-benzo[b]pyran-3-ol
(63) 6-cyano-3,4-dihydro-2,2-dimethyl-trans-4-[N-2-hydroxyethyl-(N -cyano-acetimidoyl)amino]-2H-benzo[b]pyran-3-ol The compounds of the formula (I) may be converted to pharmaceutically acceptable salts as the case requires. Such salts include, for example, salts with inorganic bases such as alkali metal salts (for example, sodium salts, potassium salts and cesium salts), alkaline earth metal salts (for example, calcium salts and magnesium salts) and ammonium salts; salts with organic bases such as organic amine salts (for example, triethylamine salts, pyridine salts, picoline salts, ethanolamine salts, triethanolamine salts, dicyclohexylamine salts and N,N-dibenzylethylenediamine salts); inorganic acid addition salts (for example, hydrochlorides, hydrobromides, sulfates and phosphates); organic carboxylic acid addition salts or organic sulfonic acid addition salts (for example, formates, acetates, trifluoroacetates, maleates, tartarates, methanesulfonates, benzenesulfonates and p-toluenesulfonates); and salts with basic amino acids or acidic amino acids (for example, arginine, aspartic acid and glutamic acid).

Further, the compounds of the formula (I) have asymmetric carbon atoms in their molecules in many cases. The benzopyran compounds of the present invention include such optical isomers and mixtures thereof.

The benzopyran compounds of the formula (I) of the present invention can be produced by the following processes.

Process 1 (process for the production of a compound of the formula (I) wherein $R^3$ is a hydrogen atom and $R^4$ is a hydroxyl group)

Such a compound can be obtained by reacting a compound of the formula (II):

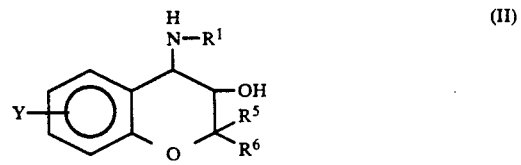
(II)

wherein $R^1$, $R^5$, $R^6$ and Y are as defined above, provided that cases wherein $R^1$ is a $R^7$—CO—, and Y is a carboxyl group, are excluded, with a compound of the formula (III):

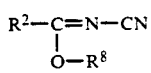
(III)

wherein $R^2$ and $R^8$ are as defined above. Here, preferred examples for $R^1$, $R^2$ and Y in the formulas (II) and (III) are as described with respect to the compounds of the formula (I). Preferred examples for $R^8$ are lower alkyl groups having from 1 to 6 carbon atoms, such as a methyl group and an ethyl group. This reaction is a condensation reaction involving a release of a lower alcohol ($R^8OH$) as shown by the following reaction formula:

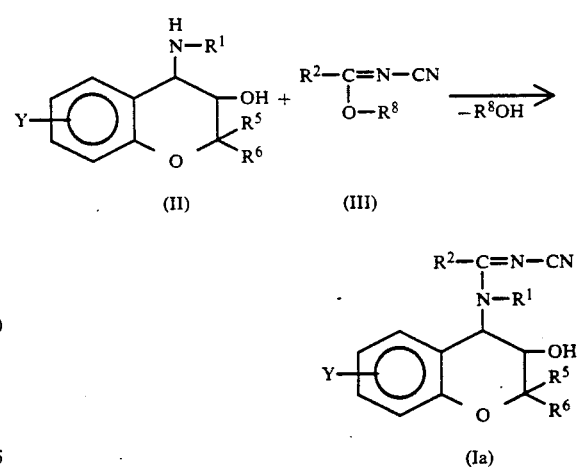

In this reaction, the reaction temperature is preferably from about 0° to 200° C., particularly from 50° to 150° C., and the reaction time is preferably from about 30 minutes to 12 hours, particularly from 1 to 6 hours. The reaction can be conducted in the presence or absence of a solvent. As the solvent, methanol, ethanol, propanol, benzene, toluene, dimethylformamide (DMF), dimethylsulfoxide (DMSO) or ethyl acetate may, for example, be employed.

Process 2 (process for the production of a compound of the formula (I) wherein $R^3$ and $R^4$ together form a bond)

Such a compound can be obtained by subjecting a compound of the formula (Ia):

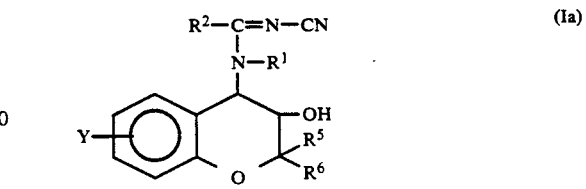
(Ia)

wherein $R^1$, $R^2$, $R^5$, $R^6$ and Y are as defined above, provided that cases wherein $R^1$ is a $R^7$—CO— group, and Y is a carboxyl group, are excluded, to dehydration treatment.

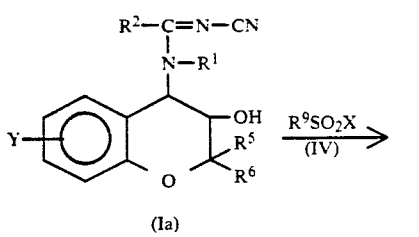

(Ia)

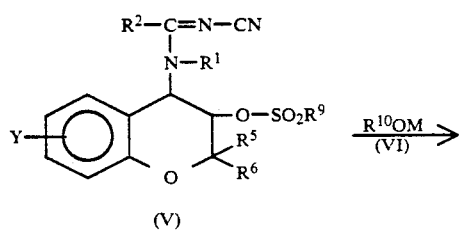

(V)

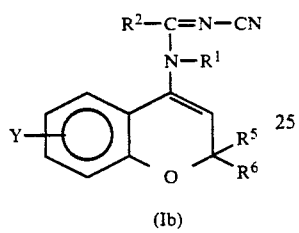

(Ib)

Namely, the reaction of the first step wherein a compound of the formula (IV) $R^9SO_2X$ is reacted to the compound of the formula (Ia), is conducted in a solvent such as pyridine, quinoline or triethylamine preferably at a temperature of from −10° to 50° C., more preferably from −5° to 10° C., preferably from 30 minutes to 12 hours, more preferably from 1 to 6 hours.

In the formula (IV), $R^9$ is an alkyl group or a substituted or unsubstituted aryl group, and X is a halogen atom. Specific compounds represented by the formula (IV) include, for example, methanesulfonyl chloride, methanesulfonyl bromide, p-toluenesulfonyl chloride and p-toluenesulfonyl bromide.

Then, the reaction of the second stage in which the resulting compound of the formula (V) is treated with a compound of the formula (VI) $R^{10}OM$ to obtain a desired compound of the formula (Ib), is conducted in a solvent such as dimethylformamide, dimethylsulfoxide, acetonitrile, benzene or toluene preferably at a temperature of from 0° to 100° C., more preferably from 20° to 40° C., preferably for from 30 minutes to 24 hours, more preferably from 3 to 12 hours.

In the formula (VI), $R^{10}$ is an alkyl group. As such an alkyl group, a methyl group, an ethyl group, a propyl group or a tert-butyl group is, for example, preferred. M is an alkali metal.

Specific compounds represented by the formula (VI) include, for example, potassium tert-butyrate, potassium ethylate, potassium methylate, sodium ethylate and sodium methylate.

Process 3 (process for the production of a compound of the formula (I) wherein $R^3$ and $R^4$ together form a bond)

A compound of the formula (Ib) can be obtained by reacting the compound of the formula (V) obtained by the above Process 2, with 1,8-diazabicyclo[5,4,0]-7-undecene in an organic solvent such as benzene.

Process 4 (process for the production of a compound of the formula (I) wherein $R^3$ and $R^4$ together form a bond)

A compound of the formula (Ib) can be obtained by subjecting the compound of the formula (Ia) to dehydration treatment by 1) reacting sodium hydride (NaH) in a solvent such as tetrahydrofuran, 2) reacting hydrochloric acid in a solvent such as ethyl alcohol, or 3) reacting p-toluene sulfonic acid in a solvent such as benzene.

Process 5 (process for the production of a compound of the formula (I) wherein $R^1$ is a substituted or unsubstituted $C_{1-6}$ alkyl group, a $C_{2-6}$ alkenyl group or $C_{2-6}$ alkynyl group, and $R^3$ and $R^4$ together form a bond)

A compound of the formula (VII):

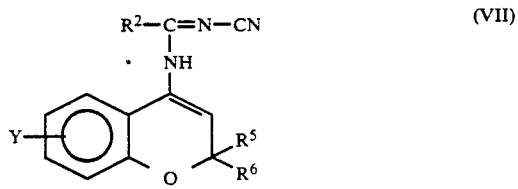

(VII)

wherein $R^2$, $R^5$, $R^6$ and Y are as defined above, is reacted with a compound of the formula (VIII):

$R^{11}$—X    (VIII)

wherein $R^{11}$ and X are as defined above, in an organic solvent such as acetonitrile, methanol, benzene or DMF in the presence of a basic compound such as potassium carbonate, sodium carbonate, triethylamine or sodium methalate, whereby a compound of the formula (Ib) wherein $R^1$ is a substituted or unsubstituted $C_{1-6}$ alkyl group, a $C_{2-6}$ alkenyl group or a $C_{2-6}$ alkynyl group, can be obtained.

Process 6 (process for the production of a compound of the formula (I) wherein $R^1$ is a $R^7$—CO— group, and $R^3$ and $R^4$ together form a bond)

A compound of the formula (VII) is reacted with a compound of the formula (IX):

$R^7$—CO—X    (IX)

wherein $R^7$ and X are as defined above, in an organic solvent such as pyridine or triethylamine, to obtain a compound of the formula (Ib) wherein $R^1$ is a $R^7$'CO— group.

Process 7 (process for the production of a compound of the formula (I) wherein Y is a carboxyl group)

A compound of the formula (I) wherein Y is a carboxyl group, can be obtained by hydrolyzing a compound of the formula (X):

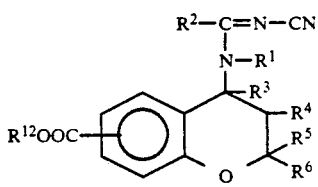

wherein $R^1$, $R^2$, $R^3$, $R^4$, $R^5$, $R^6$ and $R^{12}$ are as defined above, under a basic condition.

Process 8 (process for the production of a compound of the formula (I) wherein Y is a morpholinocarbonyl group or a di-$C_{1-6}$ alkylaminocarbonyl group)

A compound obtained by the above Process 7 (a compound of the formula (I) wherein Y is a carboxyl group) is reacted with morpholine or a dialkylamine in the presence of e.g. dicyclohexylcarbodiimide, to obtain a compound of the formula (I) wherein Y is a morpholinocarbonyl group or a di-$C_{1-6}$ alkylaminocarbonyl group.

The present invention also provides a compound of the formula (XI):

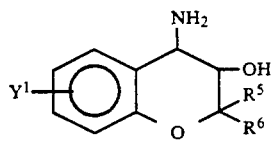

wherein $Y^1$ is a $C_{2-6}$ alkynyl group, and $R^5$ and $R^6$ are as defined above, as a starting material useful for the production of the compound of the formula (I).

The compound of the formula (XI) is a novel compound and can be produced, for example, by the reaction represented by the following formulas:

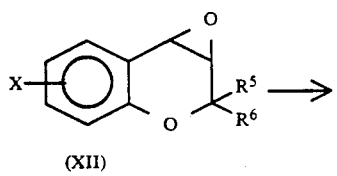

(XII)

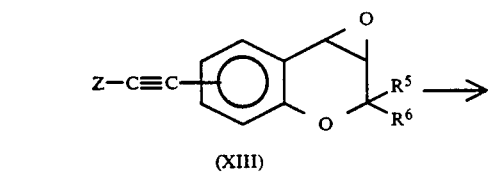

(XIII)

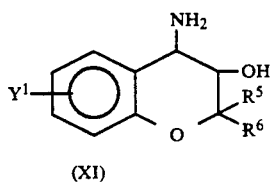

(XI)

In the above formulas, X is a halogen atom, and Z is a $C_{1-4}$ alkyl group or a trialkylsilyl group.

Specifically, to a compound of the formula (XII), a tertiary amine such as triethylamine, triphenylphosphine, palladium acetate or palladium chloride, and a $C_{3-6}$ alkyne compound or trimethylsilyl acetylene, are added and reacted in a nitrogen stream at a temperature of from 50° to 150° C. for from 6 to 24 hours to obtain a compound of the formula (XIII). Then, the compound of the formula (XIII) is dissolved in an ammonia-containing alcohol, and a reaction is conducted at a temperature of from 5° to 50° C. for from 6 to 48 hours to obtain a $C_{2-6}$ alkynyl-3,4-dihydro-2,2-dimethyl-trans-4-amino-2H-benzo[b]pyran-3-ol of the formula (XI).

The benzopyran compounds of the present invention have excellent potassium channel activating action and serve to relax various smooth muscles and improve potassium permeability through smooth muscle cell membranes. Treatments of diseases by means of such activities include prevention and treatment of e.g. hypertension, transient cerebral ischemic attack, cerebral infarction, cerebral arteriosclerosis, angina pectoris, chronic cardiac insufficiency, myocardial infarction and arrhythmia. Further, they are effective for relaxation of smooth muscles of the wind pipe, the gastro-intestinal tract, the bladder and the uterus. Accordingly, they are useful for treatment of asthma, obstructive disorders of the respiratory system, gastro-intestinal diseases and uterus diseases. Further, they are useful also for treatment of intermittent claudication.

Further, they have vasodilator activities due to the potassium channel activating action, and they are potentially useful as hair promoting agents.

The pharmaceutical compositions of the present invention may be constituted solely by the benzopyran compounds of the formula (I). However, it is usually preferred to formulate them with suitable carriers or excipients into suitable formulations for oral administration. However, they may be administered by other administration route such as a non-oral administration, for example, to a patient having a heart trouble. Drug formulations for oral administration include tablets, capsules, granules, liquids and suspensions. These drug formulations can readily be prepared in accordance with usual methods.

Pharmaceutically acceptable excipients useful for such drug formulations include, for example, gelatin, lactose, glucose, sodium chloride, starch, magnesium stearate, talc, vegetable oil as well as other pharmaceutical excipients.

The dose of the benzopyran compound of the present invention varies depending upon the administration route, the type of the formulation, the condition of the patient, etc., but is usually within a range of from 0.002 to 2 mg/kg of body weight, preferably from 0.01 to 0.2 mg/kg of body weight.

Now, the present invention will be described in further detail with reference to Examples and Test Examples. However, it should be understood that the present invention is by no means restricted by such specific Examples.

EXAMPLE 1

Preparation of 6-cyano-3,4-dihydro-2,2-dimethyl-trans-4-[(N-cyanoformimidoyl)amino]-2H-benzo[b]pyran-3-ol To 1.18 g of ethyl N-cyanoformimidate, 2.29 g of 6-cyano-3,4-dihydro-2,2-dimethyl-trans-4-amino-2H-benzo[b]pyran-3-ol was added, and the mixture was reacted under stirring at a temperature of from 100° to 120° C. for 2 hours. The reaction mixture was cooled, then dissolved in 100 ml of ethyl acetate, washed twice with a saturated sodium chloride aqueous solution and then dried over anhydrous sodium sulfate. Then, ethyl acetate was distilled off under reduced pressure. The residual solid was recrystallized from methylene chloride/isopropanol/petroleum ether to obtain 1.75 g of the above identified compound in the form of crystals.

Melting point: 155°–158° C.
NMR(CDCl$_3$)δ:
1.27(s,3H), 1.48(s,3H), 3.66(q,1H), 5.10(t,1H),
5 13(d,1H), 6.80(d,1H), 7.28–7.55(m,2H), 8.33(d,1H),
8.57–8.97(br,1H)

EXAMPLE 2

Preparation of
6-cyano-3,4-dihydro-2,2-dimethyl-trans-4-[(N-cyano-acetimidoyl)amino]-2H-benzo[b]pyran-3-ol To 1.23 g of ethyl N-cyanoacetimidate, 2.18 g of 6-cyano-3,4-dihydro-2,2-dimethyl-trans-4-amino-2H-benzo[b]pyran-3-ol was added, and the mixture was stirred at a temperature of from 100° to 120° C. for 2 hours. The reaction mixture was cooled, then dissolved in 100 ml of ethyl acetate, washed twice with a saturated sodium chloride aqueous solution and then dried over anhydrous sodium sulfate. Then, ethyl acetate was distilled off under reduced pressure. The residual oily substance was recrystallized from ethyl acetate/n-hexane to obtain 1.75 g of the above identified compound in the form of crystals.

Melting point: 240°–243° C.
NMR(CDCl$_3$)δ:
1.26(s,3H), 1.50(s,3H), 2.45(s,3H), 3.70(q,1H),
4.86(d,1H), 5.12(t,1H), 6.86(d,1H), 7.32–7.60(m,2H),
8.53(d,1H)

EXAMPLE 3

Preparation of
6-cyano-3,4-dihydro-2,2-dimethyl-trans-4-[(N-cyano-propionimidoyl)amino]-2H-benzo[b]pyran-3-ol To 1.39 g of ethyl N-cyanopropionimidate, 2.17 g of 6-cyano-3,4-dihydro-2,2-dimethyl-trans-4-amino-2H-benzo[b]pyran-3-ol was added, and the mixture was reacted under stirring at a temperature of from 100° to 120° C. for 2 hours. The reaction mixture was cooled, then dissolved in 100 ml of ethyl acetate, washed twice with a saturated sodium chloride aqueous solution and then dried over anhydrous sodium sulfate Then, ethyl acetate was distilled off under reduced pressure The residual oily substance was purified by silica gel column chromatography to obtain 1.48 g of the above identified compound in the form of crystals.

Melting point: 113°–115° C.
NMR(CDCl$_3$)δ:
1.28(s,3H), 1.52(s,3H), 2.70(q,2H), 3.75(d,1H),
4.00(br,1H), 5.12(t,1H), 6.80(d,1H), 7.29–7.61(m,2H),
7.5–7.6(br,1H)

EXAMPLE 4

Preparation of
6-cyano-3,4-dihydro-2,2-dimethyl-trans-4-[(N-cyano-valerimidoyl)amino]-2H-benzo[b]pyran-3-ol To 3.35 g of ethyl N-cyanovalerimidate, 4.37 g of 6-cyano-3,4-dihydro-2,2-dimethly-trans-4-amino-2H-benzo[b]pyran-3-ol was added, and the mixture was reacted under stirring at a temperature of from 100° to 120° C. for 2 hours. The reaction mixture was cooled, then dissolved in 100 ml of ethyl acetate, washed twice with a saturated sodium chloride aqueous solution and then dried over anhydrous sodium sulfate. Then, ethyl acetate was distilled off under reduced pressure. The residual oily substance was purified by silica gel column chromatography to obtain 1.25 g of the above identified compound as an oily substance.

NMR(CDCl$_3$)δ:
0 95(t,3H), 1.27(s,3H), 1.50(s,3H), 1.13–1.95(br,4H),
2.35(m,2H), 3.62(d,1H), 5.07(t,1H), 6.51(d,1H),
6.86(d,1H), 7.34(m,1H), 7.50(s,1H)

EXAMPLE 5

Preparation of
6-cyano-3,4-dihydro-2,2-dimethyl-trans-4-[(N-cyano-butyrimidoyl)amino]-2H-benzo[b]pyran-3-ol To 3.09 g of ethyl N-cyanobutyrimidate, 4.38 g of 6-cyano-3,4-dihydro-2,2-dimethyl-trans-4-amino-2H-benzo[b]pyran-3-ol was added, and the mixture was reacted under stirring at a temperature of from 100° to 120° C. for 2 hours. The reaction mixture was cooled, then dissolved in 100 ml of ethyl acetate, washed twice with a saturated sodium chloride aqueous solution and then dried over anhydrous sodium sulfate. Then, ethyl acetate was distilled off under reduced pressure. The residual oily substance was purified by silica gel column chromatography to obtain 3.54 g of the above identified compound in the form of crystals.

Melting point: 138°–140° C.
NMR(CDCl$_3$)δ:
1.04(t,3H), 1.27(s,3H), 1.50(s,3H), 1.75(m,2H),
2.66(t,1H), 3.75(d,1H), 5.08(t,1H), 6.80(d,1H),
7.32(m,2H), 7.82(d,1H)

EXAMPLE 6

Preparation of
6-cyano-3,4-dihydro-2,2-dimethyl-trans-4-[(N-cyano-benzimidoyl)amino]-2H-benzo[b]pyran-3-ol 1.89 g of ethyl N-cyanobenzimidate was dissolved in 5 ml of dimethylformamide, and 2.15 g of 6-cyano-3,4-dihydro-2,2-dimethyl-trans-4-amino-2H-benzo[b]pyran-3-ol was added thereto. The mixture was reacted at a temperature of from 100° to 120° C. for 2 hours. The reaction mixture was cooled, then dissolved in 100 ml of ethyl acetate, washed four times with a saturated sodium chloride aqueous solution and then dried over anhydrous sodium sulfate. Then, ethyl acetate was distilled off under reduced pressure. The residual oily substance was purified by silica gel column chromatography to obtain 1.32 g of the above identified compound in the form of crystals.

Melting point: 184°–185° C.
NMR(CDCl$_3$)δ:
1.32(s,3H), 1.51(s,3H), 3.65–3.95(m,1H),
4.45–4.75(br,1H),
5.27(t,1H), 6.80(d,1H), 7.67–7.80(m,7H),
8.10(d,1H)

EXAMPLE 7

Preparation of
6-cyano-3,4-dihydro-2,2-dimethyl-trans-4-[N-methyl-(N-cyano-acetimidoyl)amino]-2H-benzo[b]pyran-3-ol To 2.80 g of ethyl N-cyanoacetimidate, 4.65 g of 6-cyano-3,4-dihydro-2,2-dimethyl-trans-4-methylamino-2H-benzo[b]pyran-3-ol was added, and the mixture was reacted under stirring at a temperature of from 100° to 120° C. for 2 hours. The reaction mixture was cooled, then dissolved in 100 ml of ethyl acetate, washed twice with a saturated sodium chloride aqueous solution and then dried over anhydrous sodium sulfate. Then, ethyl acetate was distilled off under reduced pressure The residual solid was recrystallized from ethanol to obtain 2.34 g of the above identified compound in the form of crystals.

Melting point: 250°–251° C.
NMR(CDCl$_3$)δ:
1.29(s,3H), 1.53(s,3H), 2.60–2.91(m,6H), 3.58(q,1H), 4.88(d,1H), 5.50(d,1H), 6.80(d,1H), 6.86(d,1H), 7.20–7.63(m,2H)

EXAMPLE 8

Preparation of 6-cyano-3,4-dihydro-2,2-dimethyl-trans-4-N-butyl-(N-cyano-acetimidoyl)amino]-2H-benzo[b]pyran-3-ol To 1.13 g of ethyl N-cyanoacetimidate, 2.3 g of 6-cyano-3,4-dihydro-2,2-dimethyl-trans-4-dibutylamino-2H-benzo[b]pyran-3-ol was added, and the mixture was reacted under stirring at a temperature of from 100° to 120° C. for 2 hours. The reaction mixture was cooled, then dissolved in 100 ml of ethyl acetate, washed twice with a saturated sodium chloride aqueous solution and then dried over anhydrous sodium sulfate. Then, ethyl acetate was distilled off under reduced pressure. The residual solid was purified by silica gel chromatography to obtain 1.43 g of the above identified compound in the form of crystals.

Melting point: 163°–165° C.
NMR(CDCl$_3$)δ:
0.91(t,3H), 1.15–2.00(m,4H), 1.28(s,3H), 1.58(s,3H), 6.76–7.64(m,3H)

EXAMPLE 9

Preparation of 6-cyano-3,4-dihydro-2,2-dimethyl-trans-4-N-benzyl-(N-cyano-acetimidoyl)amino]-2H-benzo[b]pyran-3-ol To 1.54 g of ethyl N-cyanoacetimidate, 3.86 g of 6-cyano-3,4-dihydro-2,2-dimethyl-trans-4-benzylamino-2H-benzo[b]pyran-3-ol was added, and the mixture was reacted under stirring at a temperature of from 100° to 120° C. for 2 hours The reaction mixture was cooled, then dissolved in 100 ml of ethyl acetate, washed twice with a saturated sodium chloride aqueous solution and then dried over anhydrous sodium sulfate. Then, ethyl acetate was distilled off under reduced pressure The residual solid was purified by silica gel chromatography to obtain 1.65 g of the above identified compound in the form of crystals.

Melting point 201°–203° C.
NMR(CDCl$_3$)δ:
1.28(s,3H), 1.47(s,3H), 2.60(d,3H), 3.70(br,1H), 4.45(s,2H), 5.00(d,1H), 6.85(d,1H), 7.05–7.55(m,7H)

EXAMPLE 10

Preparation of 6-ethynyl-3,4-dihydro-2,2-dimethyl-trans-4-[(N-cyano-acetimidoyl)amino]-2H-benzo[b]pyran-3-ol To 1.54 g of ethyl N-cyanoacetimidate, 3.86 g of 6-cyano-3,4-dihydro-2,2-dimethyl-trans-4-benzylamino-2H-benzo[b]pyran-3-ol was added, and the mixture was reacted under stirring at a temperature of from 100° to 120° C. for 2 hours. The reaction mixture was cooled, then dissolved in 100 ml of ethyl acetate, washed twice with a saturated sodium chloride aqueous solution and then dried over anhydrous sodium sulfate. Then, ethyl acetate was distilled off under reduced pressure. The residual solid was purified by silica gel chromatography to obtain 1.65 g of the above identified compound in the form of crystals.

Melting point: 201°–203° C.
NMR(CDCl$_3$)δ:
1.28(s,3H), 1.47(s,3H), 2.60(d,3H), 3.70(br,1H), 4.45(s,2H), 5.00(d,1H), 6.85(d,1H), 7.05–7.55(m,7H)

EXAMPLE 10

Preparation of 6-ethynyl-3,4-dihydro-2,2-dimethyl-trans-4-[(N-cyano-acetimidoyl)amino]-2H-benzo[b]pyran-3-ol The reaction was conducted in the same manner as in Example 1 except that as the starting material, 6-ethynyl-3,4-dihydro-2,2-dimethyl-trans-4-amino-2H-benzo[b]pyran-3-ol was used, to obtain the above identified compound.

Melting point: 265° C. (decomposed)
NMR(DMSO-d$_6$)δ:
1.25(s,3H), 1.50(s,3H), 2.40(s,3H), 3.26(s,1H), 3 63(d,1H), 5.13(d,1H), 6.70(d,1H), 7.60–7.83(m,2H)

EXAMPLES 11 to 19

The reactions were conducted in the same manner as in Example 1 except that the starting material was changed, to obtain the following benzopyran compounds of the present invention. The compounds obtained in Examples 11 to 19 are as follows.

Example 11

6-cyano-3,4-dihydro-2,2-dimethyl-trans-4-[N-allyl-(N-cyano-acetimidoyl)amino]-2H-benzo[b]pyran-3-ol

Example 12

6-cyano-3,4-dihydro-2,2-dimethyl-trans-4-[N-propargyl-(N-cyano-acetimidoyl)amino]-2H-benzo[b]pyran-3-ol

Example 13

6-fluoro-3,4-dihydro-2,2-dimethyl-trans-4-[(N-cyano-acetimidoyl)amino]-2H-benzo[b]pyran-3-ol

Example 14

6-chloro-3,4-dihydro-2,2-dimethyl-trans-4-[(N-cyano-acetimidoyl)amino]-2H-benzo[b]pyran-3-ol

Example 15

6-methoxy-3,4-dihydro-2,2-dimethyl-trans-4-[(N-cyano-acetimidoyl)amino]-2H-benzo[b]pyran-3-ol

Example 16

6-acetyl-3,4-dihydro-2,2-dimethyl-trans-4-[(N-cyano-acetimidoyl)amino]-2H-benzo[b]pyran-3-ol

Example 17

6-nitro-3,4-dihydro-2,2-dimethyl-trans-4-[(N-cyano-acetimidoyl)amino]-2H-benzo[b]pyran-3-ol

Example 18

6-phenyl-3,4-dihydro-2,2-dimethyl-trans-4-[(N-cyano-acetimidoyl)amino]-2H-benzo[b]pyran-3-ol

Example 19

6-ethoxycarbonyl-3,4-dihydro-2,2-dimethyl-trans -4-[(N-cyano-acetimidoyl)amino]-2H-benzo[b]pyran-3-ol The melting points and the results of the NMR analyses of the benzopyran compounds obtained in Examples 1 to 19 are shown in Table 1.

TABLE 1

| Example No. | Melting point (°C.) | NMR δ (DMSO-d6) |
|---|---|---|
| 11 | 109–112 | 1.25(s, 3H), 1.50(s, 3H), 2.65(s, 3H), 2.66(d, 2H), 3.50–3.97(m, 3H), 4.72–5.42 (m, 2H), 5.60(d, 1H), 6.87(d, 1H), 7.18–7.60(m, 2H) |
| 12 | 124–127 | 1.30(s, 3H), 1.54(s, 3H), 2.54(s, 1H), 2.72(s, 3H), 3.72–4.05(m, 1H), 3.90(s, 1H), 4.95(d, 1H), 5.12(d, 1H), 6.90(d, 1H), 7.30–7.65(m, 2H) |
| 13 | 224–226 | 1.22(s, 3H), 1.44(s, 3H), 2.40(s, 3H), 3.64(dd, 1H), 5.06(t, 1H), 5.28(d, 1H), 6.47–7.14(m, 3H), 8.90(d, 1H) |
| 14 | 247–250 | 1.16(s, 3H), 1.40(s, 3H), 2.36(s, 3H), 3.57(dd, 1H), 4.98(t, 1H), 5.69(d, 1H), 6.80(d, 1H), 7.04–7.37(m, 2H), 9.10(d, 1H) |
| 15 | 207–209 | 1.13(s, 3H), 1.38(s, 3H), 2.34(s, 3H), 3.57(dd, 1H), 3.68(s, 3H), 4.95(t, 1H), 5.57(d, 1H), 6.53–6.96(m, 3H), 9.08(d, 1H) |
| 16 | 127–129 | 1.23(s, 3H), 1.50(s, 3H), 2.40(s, 3H), 2.52(s, 3H), 3.67(dd, 1H), 5.07(t, 1H), 5.72(d, 1H), 6.85(d, 1H), 7.60–7.97 (m, 2H), 9.08(d, 1H) |
| 17 | 211–213 | 1.23(s, 3H), 1.46(s, 3H), 2.37(s, 3H), 3.68(dd, 1H), 5.06(t, 1H), 5.84(d, 1H), 6.97(d, 1H), 7.81–8.25(m, 3H), 9.17(d, 1H) |
| 18 | 184–186 | 1.23(s, 3H), 1.43(s, 3H), 2.33(s, 3H), 3.66(s, 3H), 5.16(d, 1H), 6.80(d, 1H), 7.30–7.53(m, 7H) |
| 19 | 147–149 | 1.28(s, 3H), 1.48(s, 3H), 1.70–2.03 (m, 4H), 2.95(s, 1H), 2.72–3.16 (m, 4H), 3.53(d, 1H), 3.93(d, 1H), 6.67(d, 1H), 7.18(dd, 1H), 7.30(s, 1H) |

EXAMPLES 20 to 33

In the same manner as above, various benzopyran compounds of the formula (I) wherein $R^3$ is a hydrogen atom, $R^4$ is a hydroxyl group and each of $R^5$ and $R^6$ is a methyl group, were prepared. The melting points and the results of the NMR analyses of the compounds of Examples 20 to 33 are shown in Table 2.

TABLE 2

| Example No. | $R^1$ | $R^2$ | Y | Melting point (°C.) | NMR δ (DMSO-d6) |
|---|---|---|---|---|---|
| 20 | H | —Et | 6-NO2 | 212–213 | 1.27(s, 3H), 1.36(t, 3H), 1.50(s, 3H), 2.72(q, 2H), 3.78(dd, 1H), 5.10(t, 1H), 5.90(d, 1H), 7.05(d, 1H), 8.00(d, 1H), 8.17(dd, 1H), 9.23(d, 1H) |
| 21 | H | —Pr | 6-NO2 | 203–204 | 1.05(t, 3H), 1.24(s, 3H), 1.46(s, 3H), 1.81(q, 2H), 2.62(q, 2H), 3.70(dd, 1H), 5.03(t, 1H), 5.88(d, 1H), 6.97(d, 1H), 7.94(d, 1H), 8.07(dd, 1H), 9.21(d, 1H) |
| 22 | H | —CH3 | 6-Br | 276–277 | 1.15(s, 3H), 1.40(s, 3H), 2.34(s, 3H), 3.57(dd, 1H), 4.70(t, 1H), 5.75(d, 1H), 6.76(d, 1H), 7.20(d, 1H), 7.34(dd, 1H), 9.16(d, 1H) |
| 23 | H | —Et | 6-Cl | 179–180 | 1.25(s, 3H), 1.40(t, 3H), 1.48(s, 3H), 2.75(m, 2H), 3.77(m, 1H), 5.15(t, 1H), 5.21(d, 1H), 6.85(m, 1H), 7.23(m, 2H), 8.90(d, 1H) |
| 24 | H | —Et | 6-F | 158–159 | 1.15(s, 3H), 1.35(t, 3H), 1.40(s, 3H), 3.72(dd, 2H), 5.07(t, 1H), 5.42(d, 1H), 6.87(m, 3H), 8.97(d, 1H) |
| 25 | H | —Et | 6-CH3 | 180–181 | 1.14(s, 3H), 1.25(t, 3H), 1.35(s, 3H), 2.23(s, 3H), 2.67(q, 2H), 3.66(dd, 1H), 5.01(t, 1H), 5.61(d, 1H), 6.73(d, 1H), 6.96(d, 1H), 7.10(dd, 1H), 9.14(d, 1H) |
| 26 | H | —Pr | 6-CH3 | 140–141 | 1.05(t, 3H), 1.00(s, 3H), 1.40(s, 3H), 1.71(m, 2H), 2.24(s, 3H), 2.64(t, 2H), 3.62(dd, 1H), 5.03(t, 1H), 5.60(d, 1H), 6.74(d, 1H), 6.97(d, 1H), 7.06(dd, 1H), 9.14(d, 1H) |
| 27 | H | 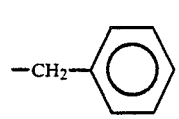 —CH2—(phenyl) | 6-NO2 | 201–204 | 1.22(s, 3H), 1.45(s, 3H), 3.72(dd, 1H), 3.92(d, 1H), 4.02(d, 1H), 5.04(m, 1H), 5.95(d, 1H), 7.00(d, 1H), 7.23–7.50(m, 5H), 7.84(dd, 1H), 8.06(dd, 1H), 9.55(brd, 1H) |

TABLE 2-continued

| Example No. | R¹ | R² | Y | Melting point (°C.) | NMR δ (DMSO-d₆) |
|---|---|---|---|---|---|
| 28 | H | —⟨phenyl⟩ | 6-NO₂ | 207–209 | 1.29(s, 3H), 1.50(s, 3H), 3.85(dd, 1H), 5.25(t, 1H), 6.05(d, 1H), 6.98(d, 1H), 7.62(m, 3H) |
| 29 | H | —⟨phenyl⟩ | 6-F | 200–201 | 1.20(s, 3H), 1.42(s, 3H), 3.76(dd, 1H), 5.16(t, 1H), 5.87(d, 1H), 6.78(dd, 1H), 6.96(d, 1H), 6.98(dd, 1H), 7.58(m, 3H), 7.76(dd, 2H), 9.40(d, 1H) |
| 30 | H | H | 6-NO₂ | 247.5–249.5 | 1.22(s, 3H), 1.45(s, 3H), 3.68(dd, 1H), 5.02(d, 1H), 5.93(d, 1H), 6.99(d, 1H), 7.95(d, 1H), 8.10(m, 1H), 8.70(s, 1H), 9.44(brs, 1H) |
| 31 | H | iso-Pen | 6-NO₂ | 213–215 | 1.02(d, 3H), 1.05(d, 3H), 1.22(s, 3H), 1.45(s, 3H), 2.24(m, 1H), 2.52(m, 2H), 3.69(d, 1H), 5.03(dd, 1H), 5.86(brs, 1H), 7.00(d, 1H), 7.96(d, 1H), 8.07(dd, 1H), 9.21(d, 1H) |
| 32 | H | iso-Pen | 6-CN | 187–189 | 1.01(d, 3H), 1.02(d, 3H), 1.20(s, 3H), 1.42(s, 3H), 2.22(m, 1H), 2.52(m, 2H), 3.63(dd, 1H), 4.99(dd, 1H), 5.75(d, 1H), 6.93(d, 1H), 7.49(s, 1H), 7.59(d, 1H), 9.06(d, 1H) |
| 33 | H | —Et | 6-Br | 192–194 | 1.18(s, 3H), 1.30(t, 3H), 1.40(s, 3H), 2.63(q, 2H), 3.60(dd, 1H), 4.95(t, 1H), 5.77(m, 1H), 6.77(d, 1H), 7.15(d, 1H), 7.34(dd, 1H), 9.12(brd, 1H) |

EXAMPLE 34

Preparation of 6-cyano-2,2-dimethyl-4-[(N-cyano-acetimidoyl)amino]-2H-benzo[b]pyran (1) 17.25 g of 6-cyano-3,4-dihydro-2,2-dimethyl-trans-4-[(N-cyano-acetimidoyl)amino]-2H-benzo[b]pyran-3-ol was dissolved in 130 ml of pyridine, and 9.0 ml of methanesulfonyl chloride was added under stirring and cooling with ice. The mixture was reacted for 4 hours. The reaction mixture was poured into ice water, whereby a solid precipitated. This solid was collected by filtration and recrystallized from ethanol to obtain 28.5 g of 6-cyano-3,4-dihydro-3-methanesulfonyloxy-2,2-dimethyl-trans-4-[(N-cyano-acetimidoyl)amino]-2H-benzo[b]pyran in the form of crystals.

Melting point: 202°–204° C.
NMR(CDCl₃)δ:
1.38(s,3H), 1,56(s,3H), 2.41(s,3H), 3.15(t,3H), 4.82(d,1H), 5.46(t,1H), 6.90(d,1H), 7.27–7.61(m,3H)

(2) Then, 9.3 g of potassium tert-butyrate was dissolved in 60 ml of dimethylformamide. Then, 0.3 g of 6-cyano-3,4-dihydro-3-methanesulfonyloxy-2,2-dimethyl-trans-4-[(N-cyano-acetimidoyl)amino]-2H-benzo[b]pyran obtained in Step (1) was added thereto, and the mixture was stirred at room temperature for 4 hours. The reaction mixture was poured into 150 ml of ice water and adjusted to a pH of from 2 to 3 with dilute hydrochloric acid. Then, the mixture was extracted with 200 ml of ethyl acetate, and the extract was washed twice with a saturated sodium chloride aqueous solution and then dried over anhydrous sodium sulfate. Then, ethyl acetate was distilled off under reduced pressure The residual solid was recrystallized from 50 ml of benzene/ethyl acetate (1/1) to obtain 1.9 g of the above identified compound in the form of crystals.

Melting point: 214°–215° C. (decomposed)
NMR(DMSO-d₆)δ:
1.50(s,3H), 2,52(s,3H), 6.23(s,1H), 6.87(d,1H), 7.48(dd,1H), 7.60(d,1H), 9.30(b,1H)

EXAMPLES 35 to 40

The following compounds were prepared in the same manner as in Example 34 except that the starting material was changed.

Example 35

6-cyano-2,2-dimethyl-4-[(N-cyano-formimidoyl) amino]-2H-benzo[b]pyran

Example 36

6-cyano-2,2-dimethyl-4-[(N-cyano-propionimidoyl)amino]-2H-benzo[b]pyran

Example 37

6-cyano-2,2-dimethyl-4-[(N-cyano-valerimidoyl)amino]-2H-benzo[b]pyran

Example 38

6-cyano-2,2-dimethyl-4-[(N-cyano-benzimidoyl)amino]-2H-benzo[b]pyran

Example 39

6-chloro-2,2-dimethyl-4-[(N-cyano-acetimidoyl)amino]-2H-benzo[b]pyran

Example 40

6-fluoro-2,2-dimethyl-4-[(N-cyano-acetimidoyl)amino]-2H-benzo[b]pyran

The melting points and the results of the NMR(DMSO-$d_6$) analyses of the compounds obtained in Examples 35 to 40 are shown in Table 3.

TABLE 3

| Example No. | Melting point (°C.) | NMR (DMSO-$d_6$) δ |
|---|---|---|
| 35 | 178–180 | 1.50(s, 6H), 6.42(s, 1H), 6.83(d, 1H), 7.45(dd, 1H), 7.65(d, 1H), 8.25(d, 1H), 9.90(br., 1H) |
| 36 | 162–164 | 1.10–1.65(m, 9H), 2.75(q, 4H), 6.13(s, 1H), 6.80(d, 1H), 7.25–7.55 (m, 2H), 8.35(br, 1H) |
| 37 | 165–167 | 0.77–2.00(m, 7H), 1.45(s, 6H), 2.70(t, 2H), 6.02(s, 1H), 6.88(d, 1H), 7.43–7.67(m, 2H), 9.78(br., 1H) |
| 38 | 266–267 | 1.53(s, 6H), 6.10(s, 1H), 6.86(d, 1H), 7.45(dd, 1H), 7.65(d, 1H), 8.25(d, 1H), 9.90(br., 1H) |
| 39 | 173–174 | 1.42(s, 6H), 2.42(s, 3H), 6.06(s, 1H), 7.10–7.45(m, 2H), 9.95(br., 1H) |
| 40 | 193–195 | 1.41(s, 6H), 2.44(s, 3H), 6.04(s, 1H), 6.76–7.27(m, 3H), 9.95(br., 1H) |

EXAMPLES 41 to 49

In the same manner, various benzopyran compounds of the formula (I) wherein $R^3$ and $R^4$ together form a bond, and each of $R^5$ and $R^6$ is a methyl group, were prepared. The melting points and the results of the NMR analyses of the compounds of Examples 41 to 49 are shown in Table 4.

TABLE 4

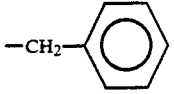

| Example No. | $R^1$ | $R^2$ | Y | Melting point (°C.) | NMR δ (DMSO-$d_6$) |
|---|---|---|---|---|---|
| 41 | H | —CH$_3$ | 6-Br | 187–189 | 1.47(s, 6H), 2.54(s, 3H), 6.26(s, 1H), 6.75(d, 1H), 7.24(d, 1H), 7.28(dd, 1H), 7.50(brs, 1H) |
| 42 | H | —CH$_3$ | 6-NO$_2$ | 203–205 | 1.50(s, 6H), 2.48(s, 3H), 6.20(s, 1H), 7.02(d, 1H), 8.03–8.15(m, 2H), 10.14(brs, 1H) |
| 43 | H | —Et | 6-NO$_2$ | 196–197 | 1.40(t, 3H), 1.50(s, 6H), 2.82(q, 2H), 6.25(s, 1H), 6.60(d, 1H), 8.17(m, 2H), 8.74(s, 1H) in CDCl$_3$ |
| 44 | H | —CH$_3$ | 6-CH$_3$ | 164–165 | 1.40(s, 6H), 2.25(s, 3H), 2.40(s, 3H), 6.00(s, 1H), 6.75(d, 1H), 6.95(d, 1H), 7.05(dd, 1H), 9.95(brs, 1H) |
| 45 | H | —Et | 6-CH$_3$ | 157–158 | 1.40(t, 3H), 1.44(s, 6H), 2.27(s, 3H), 2.74(q, 2H), 6.17(s, 1H), 6.73(d, 1H), 6.86(d, 1H), 6.97(d, 1H), 7.81(brs, 1H), in CDCl$_3$ |
| 46 | H | H | 6-NO$_2$ | 193.5–195.0 | 1.49(s, 3H), 1.50(s, 3H), 6.03, 6.47(ss, 1H), 7.02, 7.03(dd, 1H), 8.12(dd, 1H), 8.25(d, 1H), 8.58, 8.75(ss, 1H) |
| 47 | H | —Pr | 6-NO$_2$ | 203–204 | 0.86(t, 3H), 1.50(s, 3H), 1.55(s, 3H), 1.58(m, 2H), 2.28(s, 3H), 3.06(ddd, 1H), 3.98(ddd, 1H), 6.22(s, 1H), 7.08(d, 1H), 7.74(d, 1H), 8.14(dd, 1H) |
| 48 | H | —CH$_2$—C$_6$H$_5$ | 6-NO$_2$ | 195–196 | 1.51(s, 6H), 4.23(s, 2H), 6.51(s, 1H), 6.66(brs, 1H), 6.86(d, 1H), 7.28(d, 1H), 7.41(d, 2H), 7.55(m, 3H), 8.04(dd, 1H) in CDCl$_3$ |
| 49 | H | H | 6-Br | 156–158 | 1.50(s, 6H), 5.50, 6.48(ss, 1H), 6.75(dd, 1H), 7.32(m, 2H), 8.40(m, 1H), 8.55 (br, 1H) in CDCl$_3$ |

EXAMPLE 50

Preparation of 6-cyano-2,2-dimethyl-4-[(N-cyano-acetimidoyl)amino]-2H-benzo[b]pyran (1) To 15 g of 6-cyano-3,4-dihydro-3-methanesulfonyloxy-2,2-dimethyl-trans-4-[(N-cyano-acetimidoyl)amino]-2H-benzo[b]pyran obtained in Step (1) of Example 34, 300 ml of benzene and then 18 g of 1,8-diazabicyclo(5,4,0]-7-undecene were added, and the mixture was reacted under reflux for 3 hours. The reaction mixture was cooled to room temperature, then diluted by addition of 200 ml of ethyl acetate and then washed three times with water. The benzene/ethyl acetate extract solution was dried over anhydrous sodium sulfate. Then, benzene and ethyl acetate were distilled off under reduced pressure. The residual solid was recrystallized from ethanol to obtain 9.3 g of the above identified compound in the form of crystals.

Melting point: 214°-215°

EXAMPLE 51

Preparation of 6-cyano-2,2-dimethyl-4-[(N-cyano-acetimidoyl)-ethoxycarbonylmethylamino]-2H-benzo[b]pyran 6.0 g of 6-cyano-2,2-dimethyl-4-[(N-cyanoacetimidoyl)amino]-2H-benzo[b]pyran obtained in Example 34 was suspended in 200 ml of acetonitrile, and 6.12 g of potassium carbonate, 0.75 g of potassium iodide and 7.53 g of ethyl bromoacetate were added thereto. The mixture was stirred under reflux for 2 hours. Then, the reaction mixture was cooled and then filtered to remove insoluble potassium carbonate and potassium bromide The filtrate was distilled to remove acetonitrile under reduced pressure. The residue was dissolved in 250 ml of ethyl acetate, washed with a saturated sodium chloride aqueous solution, and then dried over anhydrous sodium sulfate. Then, ethyl acetate was distilled off under reduced pressure. The residual solid was recrystallized from ethyl acetate/n-hexane to obtain 4.8 g of the above identified compound in the form of crystals.

Melting point: 180.0°-182.0° C.

NMR(DMSO-$d_6$)δ:
1.31(t,3H), 1.54(s,6H), 2.36(s,3H), 3.79(d,1H), 4.24(q,2H), 4.70(d,1H), 6.08(s,1H), 6.94(d,1H), 7.31(d,1H), 7.53(dd,1H)

EXAMPLES 52 to 73

In the same manner, various benzopyran compounds of the formula (I) wherein $R^3$ and $R^4$ together form a bond, and each of $R^5$ and $R^6$ is a methyl group, were prepared. The melting points and the results of the NMR analyses of the compounds of Examples 52 to 73 are shown in Table 5.

TABLE 5

| Example No. | $R^1$ | $R^2$ | Y | Melting point (°C.) | NMR δ (DMSO-$d_6$) |
|---|---|---|---|---|---|
| 52 | —CH$_3$ | —CH$_3$ | 6-CN | 144–146 | 1.55(s, 3H), 1.58(s, 3H), 2.34(s, 3H), 3.26(s, 3H), 5.81(s, 1H), 6.98(d, 1H), 7.16(d, 1H), 7.54(dd, 1H) |
| 53 | —Et | —CH$_3$ | 6-CN | 165–167 | 1.25(t, 3H), 1.55(s, 3H), 1.60(s, 3H), 2.32(s, 3H), 3.20(m, 1H), 4.17(m, 1H), 5.72(s, 1H), 6.95(d, 1H), 7.15(d, 1H), 7.55(dd, 1H) |
| 54 | —Pr | —CH$_3$ | 6-CN | 227–230 | 0.95(t, 3H), 1.55(s, 3H), 1.60(s, 3H), 1.70(m, 2H), 2.32(s, 3H), 3.05(m, 1H), 4.07(m, 1H), 5.68(s, 1H), 6.95(d, 1H), 7.14(d, 1H), 7.55(dd, 1H) |
| 55 | —Bu | —CH$_3$ | 6-CN | 219–222 | 0.94(t, 3H), 1.34(m, 2H), 1.56(s, 3H), 1.60(s, 3H), 1.60(m, 2H), 3.07(m, 1H), 4.14(m, 1H), 5.72(s, 1H), 6.96(d, 1H), 7.14(d, 1H), 7.55(dd, 1H) |
| 56 | iso-Pr | —CH$_3$ | 6-CN | 184–186 | 1.10(d, 3H), 1.28(d, 3H), 1.56(s, 3H), 1.60(s, 3H), 2.28(s, 3H), 4.95(m, 1H), 5.67(s, 1H), 6.95(d, 1H), 7.20(d, 1H), 7.52(d, 1H) |
| 57 | iso-Bu | —CH$_3$ | 6-CN | 174–175 | 0.97(d, 6H), 1.55(s, 3H), 1.60(s, 3H), 2.02(m, 1H), 2.36(s, 3H), 2.80(dd, 1H), 4.17(dd, 1H), 5.72(s, 1H), 6.96(d, 1H), 7.12(d, 1H), 7.55(dd, 1H) |
| 58 | —CH$_2$.CH=CH$_2$ | —CH$_3$ | 6-CN | 191–192 | 1.55(s, 6H), 2.33(s, 3H), 3.70(dd, 1H), 4.79(dd, 1H), 5.24(m, 2H), 5.70(s, 1H), 5.91(m, 1H), 6.97(d, 1H), 7.19(d, 1H), 7.55(dd, 1H) |
| 59 | —CH$_2$.C≡CH | —CH$_3$ | 6-CN | 191–192.5 | 1.56(s, 3H), 1.58(s, 3H), 2.33(s, 4H), 4.18(dd, 1H), 4.76(dd, 1H), 5.89(s, 1H), 6.95(d, 1H), 7.22(s, 1H), 7.53(dd, 1H) |
| 60 | 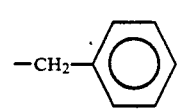 | —CH$_3$ | 6-CN | 184–186 | 1.35(s, 3H), 1.45(s, 3H), 2.34(s, 3H), 4.18(d, 1H), 5.20(s, 1H), 5.50(d, 1H), 6.92(d, 1H), 7.08(d, 1H), 7.33(br, 5H), 7.50(dd, 1H) |

TABLE 5-continued

| Example No. | R¹ | R² | Y | Melting point (°C.) | NMR δ (DMSO-d₆) |
|---|---|---|---|---|---|
| 61 | —CH₂.CH₂—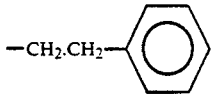 | —CH₃ | 6-CN | 187–189 | 1.43(s, 3H), 1.45(s, 3H), 2.32(s, 3H), 3.05(m, 2H), 3.30(m, 1H), 4.40(m, 1H), 5.10(s, 1H), 6.91(d, 1H), 7.07(d, 1H), 7.25(m, 5H), 7.50(dd, 1H) |
| 62 | —CH₂.COOC₂H₅ | —CH₃ | 6-CN | 180–182 | 1.31(t, 3H), 1.54(s, 6H), 2.36(s, 3H), 3.79(d, 1H), 4.24(q, 2H), 4.70(d, 1H), 6.08(s, 1H), 6.94(d, 1H), 7.31(s, 1H), 7.53(dd, 1H) |
| 63 | 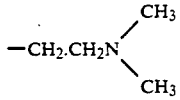 | —CH₃ | 6-CN | 192–194 | 1.54(s, 3H), 1.56(s, 3H), 2.23(s, 6H), 2.29(s, 3H), 2.53(m, 2H), 3.44(m, 1H), 4.12(m, 1H), 5.87(s, 1H), 6.93(d, 1H), 7.28(d, 1H), 7.52(dd, 1H) |
| 64 | —CH₂.CH₂OH | —CH₃ | 6-CN | 219–220.5 | 1.47(s, 3H), 1.51(s, 3H), 2.24(s, 3H), 3.23(m, 1H), 3.60(m, 2H), 4.05(m, 1H), 4.75(t, 1H), 6.15(s, 1H), 7.00(d, 1H), 7.56(d, 1H), 7.67(dd, 1H) |
| 65 | —CH₃ | —CH₃ | 6-NO₂ | 153–156 | 1.57(s, 3H), 1.60(s, 3H), 2.35(s, 3H), 3.28(s, 3H), 5.84(s, 1H), 6.99(d, 1H), 7.75(d, 1H), 8.16(dd, 1H) |
| 66 | —CH₂.CH=CH₂ | —CH₃ | 6-NO₂ | 157–158 | 1.56(s, 6H), 2.33(s, 3H), 3.72(dd, 1H), 4.78(ss, 1H), 5.18(dd, 1H), 5.27(dd, 1H), 5.72(s, 1H), 5.92(m, 1H), 6.97(d, 1H), 7.77(d, 1H), 8.15(dd, 1H) |
| 67 | —CH₂.C≡CH | —CH₃ | 6-NO₂ | 162–163 | 1.59(s, 3H), 1.61(s, 3H), 2.35(s, 3H), 4.22(dd, 1H), 4.77(dd, 1H), 5.95(s, 1H), 6.98(d, 1H), 7.85(d, 1H), 8.16(dd, 1H) |
| 68 | —CH₂.COOC₂H₅ | —CH₃ | 6-NO₂ | 171–173 | 1.31(t, 3H), 1.57(s, 6H), 2.38(s, 3H), 3.81(d, 1H), 4.25(ddq, 2H), 4.74(d, 1H), 6.13(s, 1H), 6.97(d, 1H), 7.91(d, 1H), 8.16(dd, 1H) |
| 69 | —CH₃ | H | 6-NO₂ | 187–189 | 1.57(s, 6H), 3.24(s, 3H), 5.80(s, 1H), 6.99(s, 1H), 7.85(d, 1H), 8.16(dd, 1H), 8.29(s, 1H) |
| 70 | —CH₂.CH₂OH | —CH₃ | 6-NO₂ | 228–230 | 1.52(s, 3H), 1.54(s, 3H), 2.28(s, 3H), 3.34(dt, 1H), 3.61(m, 2H), 4.08(dt, 1H), 4.79(t, 1H), 6.25(s, 1H), 7.06(d, 1H), 7.81(d, 1H), 8.13(dd, 1H) |
| 71 | —Et | —CH₃ | 6-NO₂ | 192–193 | 1.23(t, 3H), 1.57(s, 3H), 1.62(s, 3H), 2.33(s, 3H), 3.24(dt, 1H), 4.19(dt, 1H), 5.75(s, 1H), 6.98(d, 1H), 7.76(d, 1H), 8.16(dd, 1H) |
| 72 | —CH₃ | —Et | 6-NO₂ | 155–156 | 1.30(t, 3H), 1.59(s, 3H), 1.63(s, 3H), 2.19(m, 2H), 3.30(s, 3H), 5.95(s, 1H), 7.08(s, 1H), 7.85(d, 1H), 8.25(dd, 1H) in CDCl₃ |
| 73 | —CH₃ | —CH₃ | 6-Br | 166–168 | 1.50(s, 3H), 1.53(s, 3H), 2.34(s, 3H), 3.25(s, 3H), 5.69(s, 1H), 6.80(s, 1H), 6.94(d, 1H), 7.35(dd, 1H) in CDCl₃ |

EXAMPLE 74

Preparation of 6-cyano-2,2-dimethyl-4-[{(N-cyano-acetimidoyl]-N'-acetyl}amino]-2H-benzo[b]pyran 4.0 g of 6-cyano-2,2-dimethyl-4-[(N-cyanoacetimidoyl)amino]-2H-benzo[b]pyran obtained in Example 4 was dissolved in 60 ml of pyridine. To this solution, 1.77 g of acetyl chloride was dropwise added under cooling with ice. The reaction mixture was stirred for 2.5 hours under cooling with ice. Then, 250 ml of ice water was added thereto, whereby a solid precipitated. The solid was collected by filtration, washed with water and dried. This solid was recrystallized from ethyl acetate to obtain 3.4 g of the above identified compound in the form crystals.

Melting point: 214.5°-216° C.

NMR(DMSO-$d_6$)δ:
1.56(s,6H), 2.29(s,3H), 2.91(s,3H), 5.71(s,1H), 6.90(s,1H), 7.03(d,1H), 7.51(dd,1H)

EXAMPLES 75 to 81

In the same manner, various benzopyran compounds of the formula (I) wherein $R^3$ and $R^4$ together form a bond, and each of $R^5$ and $R^6$ is a methyl group, were prepared. The melting points and the results of the NMR analyses of the compounds of Examples 75 to 81 are shown in Table 6.

EXAMPLE 82

Preparation of 6-carboxy-4-[(N-cyanoacetimidoyl)amino]-2,2-dimethyl-2H-1-benzo[b]pyran 5 g (16.7 mmol) of 6-methoxycarbonyl-4-[(N-cyanoacetimidoyl)amino]-2,2-dimethyl-2H-1-benzo[b]pyran was dissolved in 200 ml of methanol, and the solution was cooled to 0° C. To this solution, 60 ml of a saturated lithium hydroxide aqueous solution was added, and the mixture was stirred at room temperature for 17 hours. The reaction mixture was poured into 400 ml of a 25% sodium dihydrogen phosphate aqueous solution and neutralized, and then extracted with 1 l of ethyl acetate. The extract solution was washed sequentially with water and a saturated sodium chloride aqueous solution and then dried over anhydrous sodium sulfate. The solvent was distilled off. The obtained-white powder was washed with ethyl acetate/hexane (5/1) and dried to obtain 4.7 g (yield: 98%) of 6-carboxy-4-[(N-cyanoacetimidoyl)amino]-2,2-dimethyl-2H-1-benzo[b]pyran.

Melting point: 194°-196° C.

NMR(DMSO-$d_6$)δ:
1.40(6H,s), 2.40(s,3H), 6.08(s,1H), 6.98(d,1H), 7.82(s,1H), 7.92(dd,1H)

TABLE 6

| Example No. | $R^1$ | $R^2$ | Y | Melting point (°C.) | NMR δ (DMSO-$d_6$) |
|---|---|---|---|---|---|
| 75 | —CO—CH$_3$ | —CH$_3$ | 6-CN | 214.5–216 | 1.56(s, 6H), 2.29(s, 3H), 2.91(s, 3H), 5.71(s, 1H), 6.90(s, 1H), 7.03(d, 1H), 7.51(dd, 1H) |
| 76 | —CO—Pr | —CH$_3$ | 6-CN | 170.5–172.5 | 0.91(t, 3H), 1.556(s, 3H), 1.563(s, 3H), 1.66(m, 2H), 2.30(m, 1H), 2.64(m, 1H), 2.91(s, 3H), 5.69(s, 1H), 6.95(d, 1H), 7.01(d, 1H), 7.51(dd, 1H) |
| 77 | —CO—CH=CH— | —CH$_3$ | 6-CN | 229–231 | 1.53(s, 3H), 1.58(s, 3H), 2.96(s, 3H), 5.74(s, 1H), 6.60(d, 1H), 6.98(d, 1H), 7.11(d, 1H), 7.40(m, 5H), 7.52(dd, 1H), 7.87(d, 1H) |
| 78 | —CO—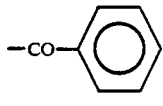 | —CH$_3$ | 6-CN | 198.5–200 | 0.93(s, 3H), 1.46(s, 3H), 2.85(s, 3H), 5.40(s, 1H), 6.88(s, 1H), 7.27–7.62(m, 7H) |
| 79 | —CO—OEt | —CH$_3$ | 6-CN | 199.5–200.5 | 1.21(t, 3H), 1.51(s, 3H), 1.54(s, 3H), 2.97(s, 3H), 4.26(q, 2H), 5.60(s, 1H), 6.90(d, 1H), 6.97(d, 1H), 7.46(dd, 1H) |
| 80 | —CO—CH$_3$ | —CH$_3$ | 6-NO$_2$ | 192–193 | 1.51(s, 3H), 1.52(s, 3H), 2.31(s, 3H), 2.81(s, 3H), 7.07(d, 1H), 7.96(d, 1H), 8.11(dd, 1H) |
| 81 | —CO—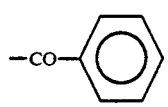 | —CH$_3$ | 6-NO$_2$ | 188–189 | 0.94(s, 3H), 1.49(s, 3H), 2.88(s, 3H), 5.46(s, 1H), 6.90(d, 1H), 7.38(t, 2H), 7.54(t, 1H), 7.63(d, 2H), 7.90(d, 1H), 8.12(dd, 1H) in CDCl$_3$ |

EXAMPLE 83

Preparation of 6-(4-morpholino)carbonyl-4-[(N-cyanoacetimidoyl)amino]-2,2-dimethyl-2H-1-benzo[b]pyran 5.6 g (19.6 mmol) of 6-carboxy-4-[(N-cyanoacetimidoyl)amino]-2,2-dimethyl-2H-1-benzo[b]pyran was dissolved in a solvent mixture comprising 120 ml of tetrahydrofuran and 120 ml of acetonitrile, and the solution was cooled to 0° C. To this solution, 8.0 g (39.3 mmol) of dicyclohexylcarbodiimide was added, and the mixture was stirred for 15 minutes. Then, 5.1 g (58.9 mmol) of morpholine was added thereto, and the mixture was stirred at room temperature for further 4 hours. The reaction mixture was diluted with 500 ml of ethyl acetate, then sequentially washed with water, a 30% sodium dihydrogen phosphate aqueous solution and a saturated sodium chloride aqueous solution and then dried over anhydrous sodium sulfate. The solvent was distilled off. Then, the residue was purified by silica gel column chromatography (developing solvent: ethyl acetate, silica gel: 150 g) to obtain 3.6 g (yield: 52.%) of 6-(4-morphilino)carbonyl-4-[(N-cyanoacetimidoyl)amino]-2,2-dimethyl-2H-1-benzo[b]pyran as white powder.

Melting point: 126°–128° C.
NMR(DMSO-$d_6$)δ:
1.44(s,6H), 2.42(s,3H), 3.49(br,s,4H), 3.60(br,s,4H),
5.96(s,1H), 6.86(d,1H), 7.18(d,1H), 7.25(dd,1H),
10.06(br,s,1H)

EXAMPLE 84

Preparation of 6-(diethylamino)carbonyl-4-[(N-cyanoacetimidoyl)amino]-2,2-dimethyl-2H-1-benzo[b]pyran In the same manner as in Example 83, the above identified compound was prepared. The melting point and the results of the NMR analysis of this compound are as follows.

Melting point: 184°–186° C.
NMR(DMSO-$d_6$)δ:
1.15(t,6H), 1.43(s,6H), 2.54(s,3H), 3.34(m,4H),
6.00(s,1H), 6.64(d,1H), 6.84(d,1H), 6.97(dd,1H),
9.79(s,1H)

EXAMPLE 85

Preparation of 6-methoxycarbonyl-4-[(N-cyanoacetimidoyl)amino]-2,2-dimethyl-2H-1-benzo[b]pyran In the same manner as in Examples 19 and 34, the above identified compound was prepared. The melting point and the results of the NMR analysis of this compound are as follows.

Melting point: 193°–195° C.
NMR(DMSO-$d_6$)δ:
1.49(s,6H), 2.54(s,3H), 3.84(s,3H), 6.32(s,1H),
6.85(d,1H), 7.82(m,2H)

EXAMPLE 86

Preparation of 6-ethynyl-3,4-dihydro-2,2-dimethyl-trans-4-amino-2H-benzo[b]pyran-3-ol (starting material of Example 10)

1) To 35 ml of triethylamine, 100 mg of palladium acetate and 200 mg of triphenylphosphine were added. To this reaction solution, 10.0 g of 6-bromo-3,4-epoxy-2,2-dimethyl-2H-benzo[b]pyran and then 6.5 g of trimethylsilyl acetylene were added, and then the mixture was reacted in a nitrogen stream at a temperature of from 70° to 85° C. for 12 hours. The reaction mixture was concentrated under reduced pressure and then dissolved in 300 ml of ethyl acetate. The solution was washed with water and the dried over anhydrous sodium sulfate. Then, ethyl acetate was distilled off under reduced pressure. The residue was purified by silica gel chromatography to obtain 10.0 g of 6-(2'-trimethylsilyl)ethynyl-3,4-epoxy-2,2-dimethyl-2H-benzo[b]pyran as an oily substance.

NMR(CDCl$_3$)δ:
0.23(s,9H), 1.20(s,3H), 1.53(s,3H), 3.40(d,1H),
3.80(d,1H), 6.63(d,1H), 7.20(d,1H), 7.43(d,1H)

10.0 g 6-(2-trimethylsilyl)ethynyl-3,4-epoxy-2,2-dimethyl-2H-benzo[b]pyran was dissolved in 500 ml of a methanol solution of saturated ammonia. The solution was left to stand at room temperature for 7 days and then concentrated under reduced pressure. The residue was purified by silica gel chromatography to obtain 5.5 g of the above identified compound.

NMR(CDCl$_3$)δ:
1.20(s,3H), 1.50(s,3H), 2.23(br,3H), 2.97(s,1H),
3.31(d,1H), 3.61(d,1H), 7.16(dd,1H), 7.53(d,1H)

Now, the pharmacological activities of the compounds of the present invention will be described with reference to Test Examples.

TEST EXAMPLE 1

Potassium channel activating action

The aorta of a male Wister rat having a body weight of about 240 g was extracted and formed into a spiral specimen, which was suspended under a load of 0.5 g in a Krebs.Henselate solution (37° C.) saturated with a gas mixture of 95% oxygen+5% carbon dioxide. Then, 20 mM or 60 mM potassium chloride was added thereto, and the contraction reaction was measured by means of an isometric transducer (manufactured by Nippon Koden K.K.). When the contraction reaction by potassium chloride reached the maximum, a compound of the present invention was cumulatively added, whereupon the relaxation reaction was measured. The relaxation reaction due to the drug was determined as a relaxation rate relative to the maximum contraction by potassium chloride. The results are shown in Table 7.

TABLE 7

| Potassium channel activating action | | | |
|---|---|---|---|
| Compound No. | Concentration (mol) | Relaxation rate (%) in 20 mM KCl | Relaxation rate (%) in 60 mM KCl |
| Example 2 | $10^{-8}$ | 6.8 | 0 |
| | $10^{-7}$ | 30.6 | 0 |
| | $10^{-6}$ | 95.6 | 1.0 |
| | $10^{-5}$ | 100 | 5.6 |
| Example 34 | $10^{-8}$ | 28.7 | 0 |
| | $10^{-7}$ | 94.3 | 4.5 |
| | $10^{-6}$ | 100 | 13.2 |
| | $10^{-5}$ | 100 | 21.8 |

TEST EXAMPLE 2

Blood pressure lowering activity

A male spontaneously hypertensive rat (SHR) of 20 weeks old was put in a cage and heated in a heating box at 45° C. for 5 minutes. SHR heated for 5 minutes was fixed to a measuring board, and a cuff for pressurizing and for blood pressure measurement was attached to the tail. As the pressurizing started, the heart rate was measured. After the rat became quiet, the maximum blood pressure was measured.

On the other hand, a compound of the present invention was dissolved or suspended in a 0.5% methyl cellulose solution and orally administered. Then, the blood pressure was measured upon expiration of 1 hour, 3 hours and 6 hours after the administration.

The change from the value prior to the administration (%) =

$$\frac{\text{Blood pressure before administration} - \text{Blood pressure after administration}}{\text{Blood pressure before administration}} \times 100$$

The results are shown in Table 8.

TABLE 8

| Compound No. | Dose (mg/kg) | Blood pressure lowering activities Change (%) from the value before administration | | |
|---|---|---|---|---|
| | | 1 hr later | 3 hrs later | 6 hrs later |
| Example 2 | 10 | 64 | 61 | 61 |
| | 3 | 60 | 56 | 58 |
| | 1 | 42 | 45 | 26 |
| | 0.3 | 26 | 17 | 12 |
| | 0.1 | 10 | 5 | 0 |
| Example 34 | 10 | 64 | 64 | 65 |
| | 3 | 65 | 63 | 63 |
| | 1 | 62 | 60 | 57 |
| | 0.3 | 41 | 45 | 23 |
| | 0.1 | 12 | 5 | 0 |
| Comparative drug Nicardipin | 10 | 40 | 9 | 7 |
| | 3 | 20 | 8 | 0 |

Action for relaxation of the tracheal smooth muscle

By a usual method, the tracheal smooth muscle of a Hartley male guinia pig was extracted and vertically suspended with a load of 0.3 g in a 2 ml Magnus bath filled with Tyrode solution at 37° C. bubbled with a gas mixture of 95% oxygen and 5% carbon dioxide. After the spontaneous tension became steady, a compound of the present invention was cumulatively added from $10^{-8}$M (final concentration), and the action was observed for about 10 minutes at each concentration. Finally, $10^{-6}$ g/ml (final concentration) of isoproterenol was added to obtain the maximum relaxation. Then, relaxation rate was determined by the following formula:

Relaxation rate (%) =

$$\frac{\text{Relaxation length (cm) by the tested compound}}{\text{The maximum relaxation length (cm) by } 10^{-6} \text{ g/ml of isoproterenol}} \times 100$$

The results are shown in Table 9.

TABLE 9

| | Activity for relaxation of the tracheal smooth muscle | |
|---|---|---|
| Compound No. | Dose (mol) | Relaxation rate (%) |
| Example 2 | $10^{-7}$ | 0 |
| | $3 \times 10^{-7}$ | 0 |
| | $10^{-6}$ | 20.7 |
| | $3 \times 10^{-6}$ | 41.6 |
| | $10^{-5}$ | 67.5 |
| | $3 \times 10^{-5}$ | 68.2 |
| Example 34 | $10^{-7}$ | 0 |
| | $3 \times 10^{-7}$ | 10.5 |
| | $10^{-6}$ | 52.3 |

TABLE 9-continued

| | Activity for relaxation of the tracheal smooth muscle | |
|---|---|---|
| Compound No. | Dose (mol) | Relaxation rate (%) |
| | $3 \times 10^{-6}$ | 74.8 |
| | $10^{-5}$ | 80.2 |
| | $3 \times 10^{-5}$ | 82.1 |

TEST EXAMPLE 3

Toxicity test

For an acute toxicity test, ten male mice with body weights of 22 to 25 g were used as one group, and a compound of the present invention was orally administered at a dose corresponding to the body weight. From the mortality after 72 hours, LD$_{50}$ was calculated by an area method.

LD$_{50}$ of the compounds of the present invention obtained in Examples 2 and 34 was at least 2,000 mg/kg.

Now, Formulation Example will be described.

FORMULATION EXAMPLE 1

Preparation of tablets

Using the following components, tablets were prepared by a usual method.

| | |
|---|---|
| Active ingredient (Compound of the present invention obtained in Example 2) | 2 mg |
| Lactose | 150 mg |
| Crystalline cellulose | 100 mg |
| Magnesium stearate | 3 mg |

As described in detail in the foregoing, the present invention provides benzopyran compounds having excellent potassium channel activating action, which are useful for treatment of various diseases, processes for their production and pharmaceutical compositions containing such benzopyran compounds.

We claim:

1. A compound of the formula (I):

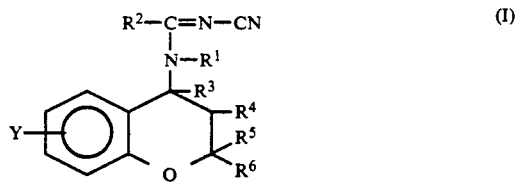

or a pharmaceutically acceptable salt thereof, wherein:
R$^1$ is a hydrogen atom, a substituted or unsubstituted C$_{1-6}$ alkyl group, a C$_{2-6}$ alkenyl group, a C$_{2-6}$ alkynyl group or a R$^7$—CO— group (wherein R$^7$ is a C$_{1-6}$ alkyl group, a phenyl group, a C$_{2-6}$ alkenyl group which may be substituted by a phenyl group, or a C$_{1-6}$ alkoxy group);
wherein the substituent of the substituted C$_{1-6}$ alkyl group for R$^1$ is a C$_{1-6}$ alkoxy group, an aryl group, a hydroxyl group, a C$_{1-6}$ alkoxycarbonyl group, or a Di-C$_{1-6}$ alkylamino group; wherein said aryl group is a phenyl group, a naphthyl group, or a xylyl group;
R$^2$ is a hydrogen atom, a substituted or unsubstituted C$_{1-8}$ alkyl group, or a phenyl group;

wherein the substituent of the substituted $C_{1-8}$ alkyl group for $R^2$ is a $C_{1-6}$ alkoxy group or an aryl group; wherein said aryl group is a phenyl group, a naphthyl group, or a xylyl group;

$R^3$ is a hydrogen atom, and $R^4$ is a hydroxyl group, or $R^3$ and $R^4$ together form a bond;

each of $R^5$ and $R^6$ is a $C_{1-4}$ alkyl group; and

Y is a cyano group, a halogen atom, a nitro group, a $C_{1-6}$ alkyl group, a $C_{2-6}$ alkynyl group, a $C_{1-6}$ alkylcarbonyl group, a $C_{1-6}$ alkoxy group, a di-$C_{1-6}$ alkylaminocarbonyl group, an aryl group, a $C_{1-6}$ alkoxycarbonyl group, a carboxyl group or a morpholinocarbonyl group; wherein said aryl group is a phenyl group, a naphthyl group, or a xylyl group.

2. The compound of claim 1, wherein the $C_{1-6}$ alkoxy substituent of the substituted $C_{1-6}$ alkyl group for $R^1$ is selected from the group consisting of methoxy, ethoxy, propoxy, iso-propoxy, n-butoxy, sec-butoxy, tert-butoxy, pentyloxy, and hexyloxy.

3. The compound of claim 1 wherein the $C_{1-6}$ alkoxycarbonyl substituent of the substituted $C_{1-6}$ alkyl group for $R^1$ is selected from the group consisting of methoxycarbonyl, ethoxycarbonyl, propoxycarbonyl, iso-propoxycarbonyl, n-butoxycarbonyl, sec-butoxycarbonyl, tert-butoxycarbonyl, pentyloxycarbonyl, and hexyloxycarbonyl.

4. The compound of claim 1 wherein the di-$C_{1-6}$ alkylamino substituent of the substituted $C_{1-6}$ alkyl group for $R^1$ contains $C_{1-6}$ alkyl groups selected from the group consisting of methyl, ethyl, propyl, iso-propyl, n-butyl, sec-butyl, tert-butyl, pentyl, and hexyl.

5. The compound of claim 1 wherein the $C_{1-6}$ alkoxy group substituent of the substituted $C_{1-8}$ alkyl group for $R^2$ is selected from the group consisting of methoxy, ethoxy, propoxy, iso-propoxy, n-butoxy, sec-butoxy, tert-butoxy, pentyloxy, and hexyloxy.

6. The compound or the pharmaceutically acceptable salt thereof according to claim 1, wherein the formula (I), $R^1$ is a hydrogen atom; $R^2$ is $C_{1-8}$ alkyl group or a phenyl group; $R^3$ is a hydrogen atom and $R^4$ is a hydroxyl group, or $R^3$ or $R^4$ together form a bond; each of $R^5$ and $R^6$ is a $C_{1-4}$ alkyl group; and Y is a cyano group or a nitro group.

7. The compound or the pharmaceutically acceptable salt thereof according to claim 1, which is 6-cyano-3,4-dihydro-2,2-dimethyl-trans-4-[(N-cyano-acetimidoyl)amino]-2H-benzo[b]pyran-3-ol or a pharmaceutically acceptable salt thereof, 6-cyano -3,4-dihydro-2,2-dimethyl-trans-4-[(N -cyano-benzimidoyl)amino]-2H-benzo[b]pyran-3-ol or a pharmaceutically acceptable salt thereof, 6-nitro-3,4-dihydro-2,2-dimethyl-trans -4-[(N-cyano-acetimidoyl)amino]-2H-benzo[b]pyran-3-ol or a pharmaceutically acceptable salt thereof, 6-cyano-2,2-dimethyl-4-[(N-cyano -acetimidoyl)amino]-2H-benzo[b]pyran or a pharmaceutically acceptable salt thereof, 6-cyano-2,2-dimethyl-4-[(N-cyano-propionimidoyl)amino]-2H-benzo[b]pyran or a pharmaceutically acceptable salt thereof, or a 6-nitro-2,2-dimethyl-4-[(N-cyano-acetimidoyl)amino]-2H-benzo[b]pyran or a pharmaceutically acceptable salt thereof.

8. A pharmaceutical composition having potassium channel activating action, which comprises, as an active ingredient, a compound of the formula (I):

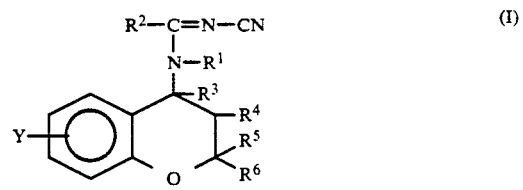

or a pharmaceutical acceptable salt thereof, wherein:

$R^1$ is hydrogen atom, a substituted or unsubstituted $C_{1-6}$ alkyl group, a $C_{2-6}$ alkenyl group, a $C_{2-6}$ alkynyl group or a $R^7$—CO— group (wherein $R^7$ is a $C_{1-6}$ alkyl group, a phenyl group, a $C_{2-6}$ alkenyl group which may be substituted by a phenyl group, or a $C_{1-6}$ alkoxy group);

wherein the substituent of the substituted $C_{1-6}$ alkyl group for $R^1$ is a $C_{1-6}$ alkoxy group, an aryl group, a hydroxyl group, a $C_{1-6}$ alkoxycarbonyl group, or a di-$C_{1-6}$ alkylamino group; wherein said aryl group is a phenyl group, a naphthyl group, or a xylyl group;

$R^2$ is a hydrogen atom, a substituted or unsubstituted $C_{1-8}$ alkyl group, or a phenyl group;

wherein the substituent of the substituted $C_{1-8}$ alkyl group for $R^2$ is a $C_{1-6}$ alkoxy group or an aryl group; wherein said aryl group is a phenyl group, a naphthyl group, or a xylyl group;

$R^3$ is a hydrogen atom, and $R^4$ is a hydroxyl group, or $R^3$ and $R^4$ together form a bond;

each of $R^5$ and $R^6$ is a $C_{1-4}$ alkyl group; and

Y is a cyano group, a halogen atom, a nitro group, a $C_{1-6}$ alkyl group, a $C_{2-6}$ alkynyl group, a $C_{1-6}$ alkylcarbonyl group, a $C_{1-6}$ alkoxy group, a di-$C_{1-6}$ alkylaminocarbonyl group, an aryl group, a $C_{1-6}$ alkoxycarbonyl group, a carboxyl group or a morpholinocarbonyl group; wherein said aryl group is a phenyl group, a naphthyl group, or a xylyl group; and a pharmaceutically acceptable carrier.

* * * * *